United States Patent
Winter et al.

(10) Patent No.: US 8,440,825 B2
(45) Date of Patent: May 14, 2013

(54) FUMARIC ACID SALT OF VARENICLINE

(75) Inventors: Stephen Benedict David Winter, Barcelona (ES); Monica Benito Velez, Barcelona (ES)

(73) Assignee: Medichem S.A., Barcelona (ES)

( * ) Notice: Subject to any disclaimer, the term of this patent is extended or adjusted under 35 U.S.C. 154(b) by 0 days.

(21) Appl. No.: 12/920,923

(22) PCT Filed: Mar. 6, 2009

(86) PCT No.: PCT/EP2009/052654
§ 371 (c)(1),
(2), (4) Date: Dec. 13, 2010

(87) PCT Pub. No.: WO2009/109651
PCT Pub. Date: Sep. 11, 2009

(65) Prior Publication Data
US 2011/0105750 A1    May 5, 2011

Related U.S. Application Data

(60) Provisional application No. 61/068,384, filed on Mar. 6, 2008, provisional application No. 61/123,382, filed on Apr. 8, 2008.

(51) Int. Cl.
*C07D 495/00*    (2006.01)

(52) U.S. Cl.
USPC ............................................................ 544/345

(58) Field of Classification Search .................. 544/345
See application file for complete search history.

(56) References Cited

U.S. PATENT DOCUMENTS 7,265,119 B2 *   9/2007   Bogle et al. ................... 514/250

FOREIGN PATENT DOCUMENTS

| WO | WO 02/092089 | 11/2002 |
| WO | WO 02/092597 | 11/2002 |
| WO | WO 03/045394 | 6/2003 |

* cited by examiner

*Primary Examiner* — Douglas M Willis

(74) *Attorney, Agent, or Firm* — Cozen O'Connor

(57) ABSTRACT

This invention provides a novel dicarboxylic acid salt forms of varenicline, namely varenicline fumarate, and methods for making same. Varenicline salts are useful for treating smoking addition. In one embodiment of the instant invention, the varenicline fumarate shows an XRD pattern (2θ)) (±0.2° having characteristic peaks at 10.6, 11.9, 13.2, 16.2, 16.6, 18.0, 21.5, 22.6, 25.7, 28.5 and 29.1°. In another embodiment, the varenicline fumarate is prepared by (i) contacting varenicline with fumaric acid, optionally in the presence of a suitable solvent, and removing the solvent when necessary, or (ii) contacting varenicline fumarate salt with a suitable solvent, and removing the solvent.

4 Claims, 28 Drawing Sheets

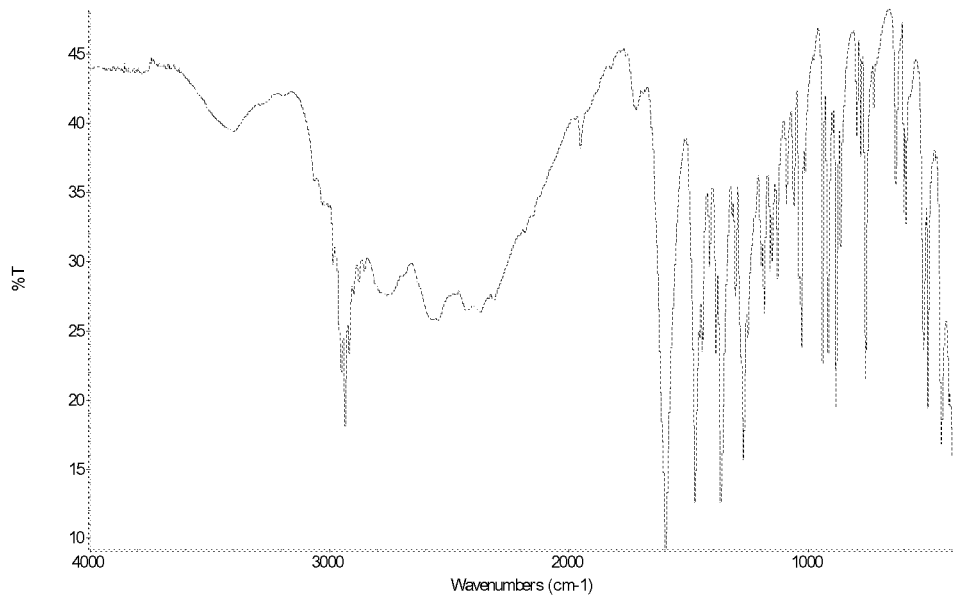
Figure 1 (IR Varenicline hemi-adipate Form I)
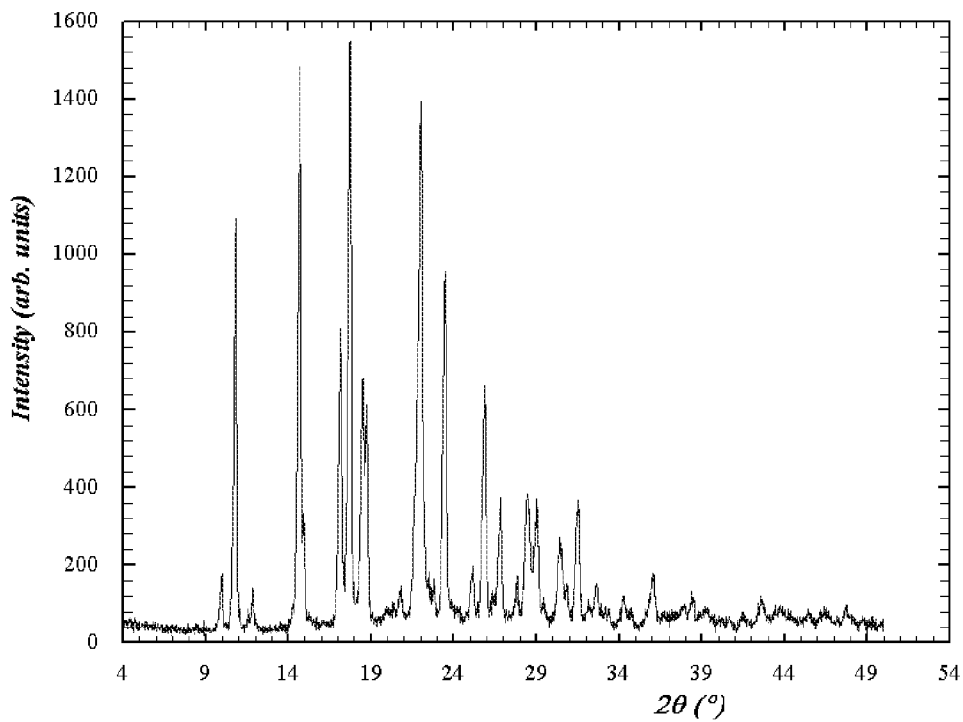
Figure 2 (XRD Varenicline hemi-adipate Form I)

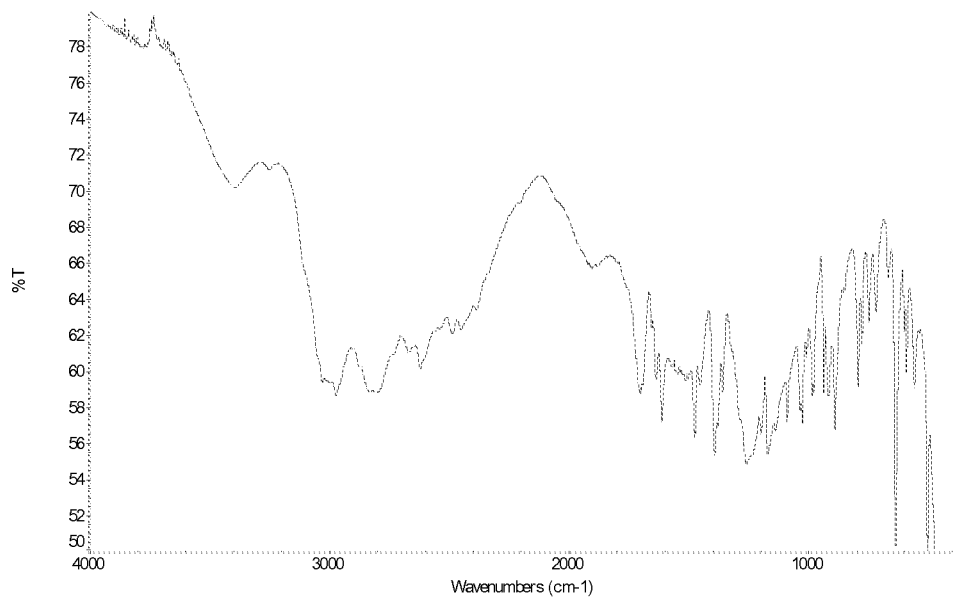
Figure 3 (IR Varenicline fumarate Form I)
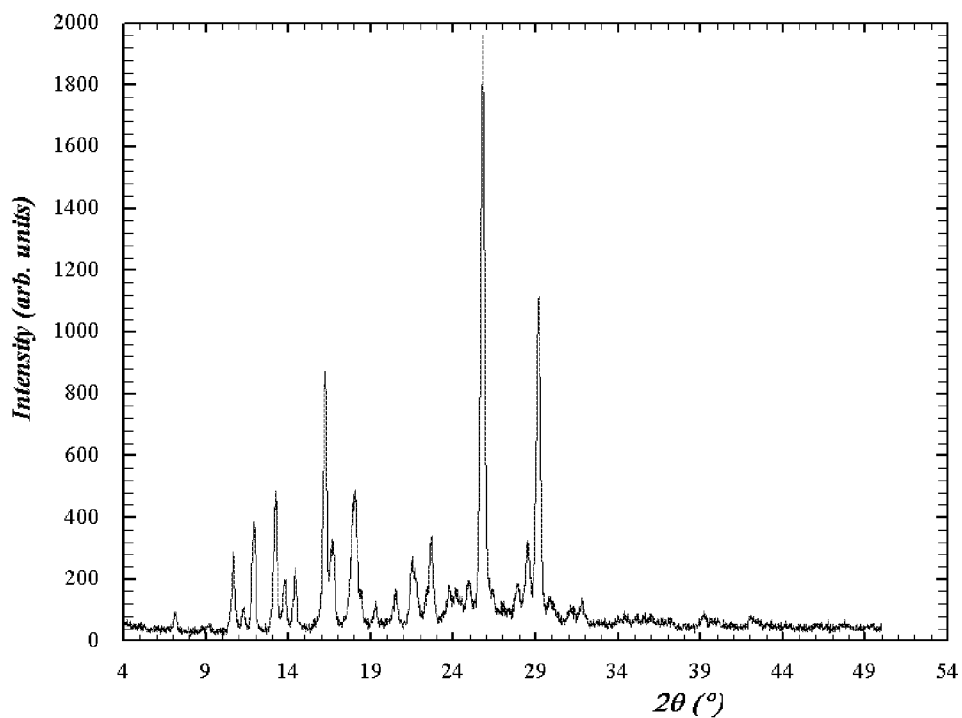
Figure 4 (XRD Varenicline fumarate Form I)

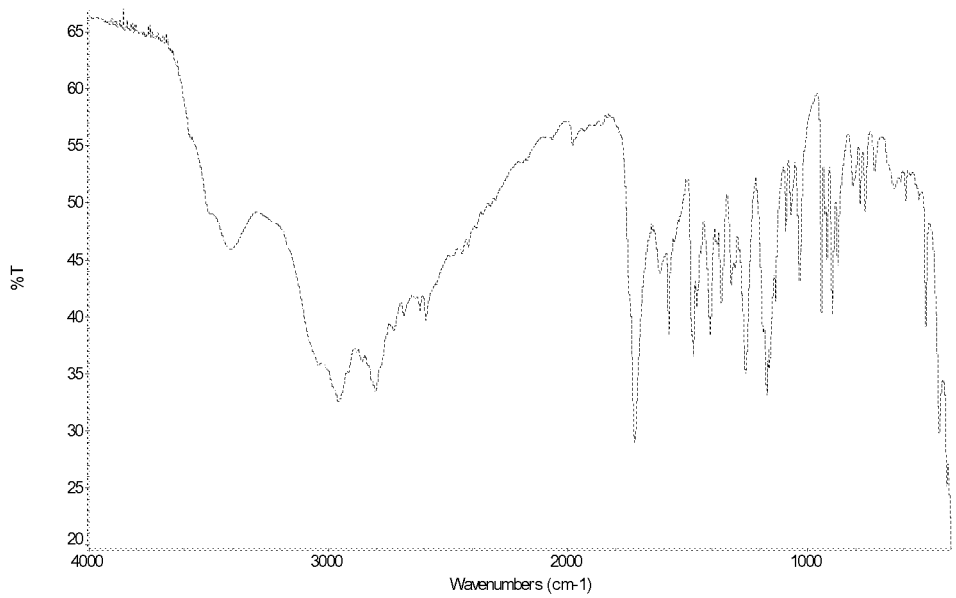
Figure 5 (IR Varenicline glutarate Form I)
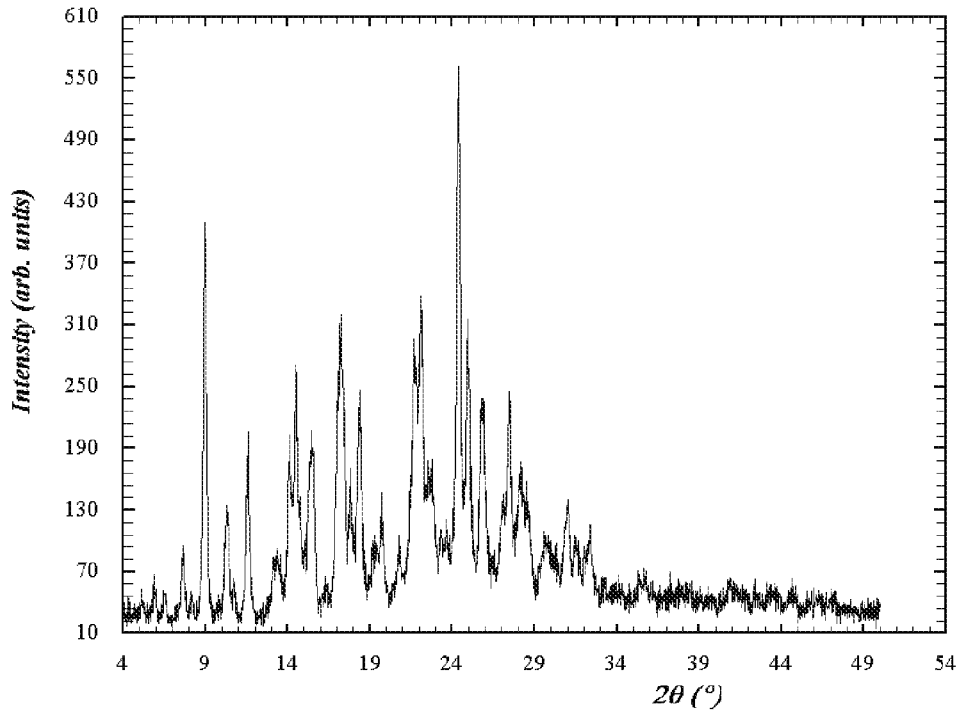
Figure 6 (XRD Varenicline glutarate Form I)

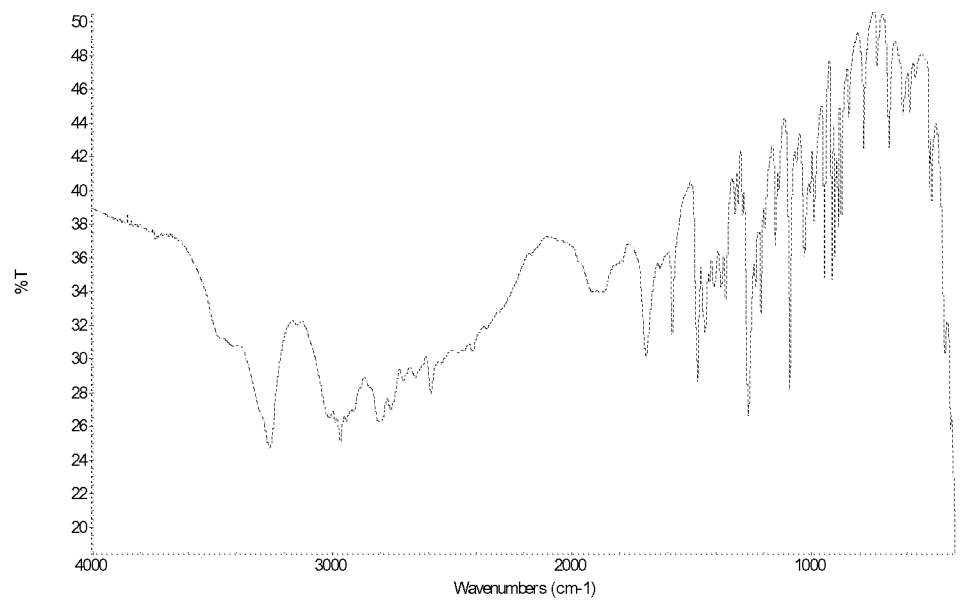
Figure 7 (IR Varenicline glycolate Form I)
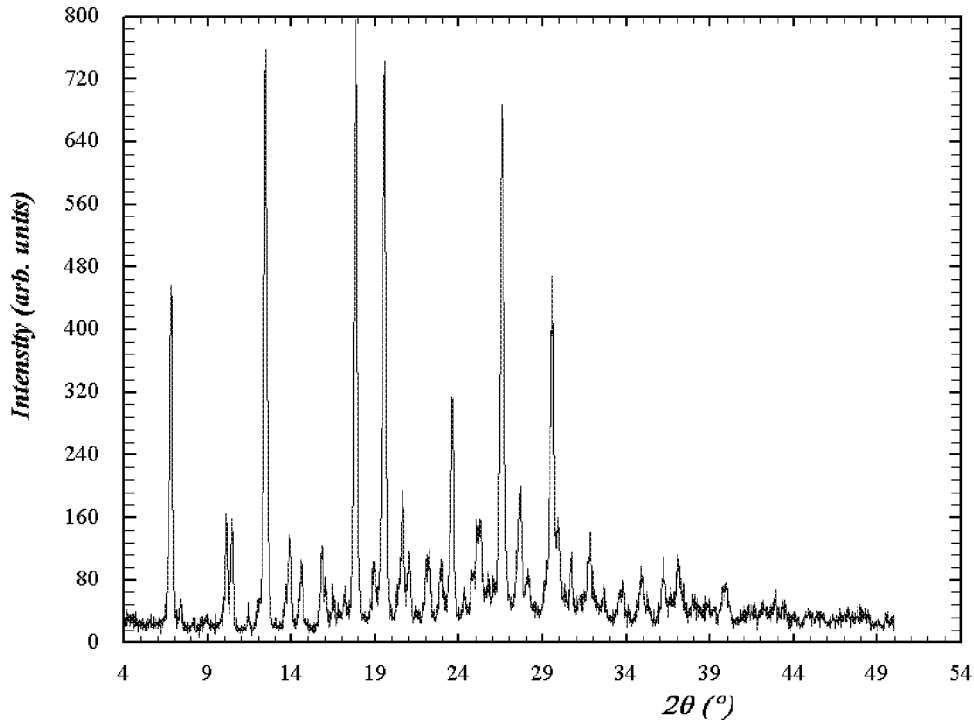
Figure 8 (XRD Varenicline glycolate Form I)

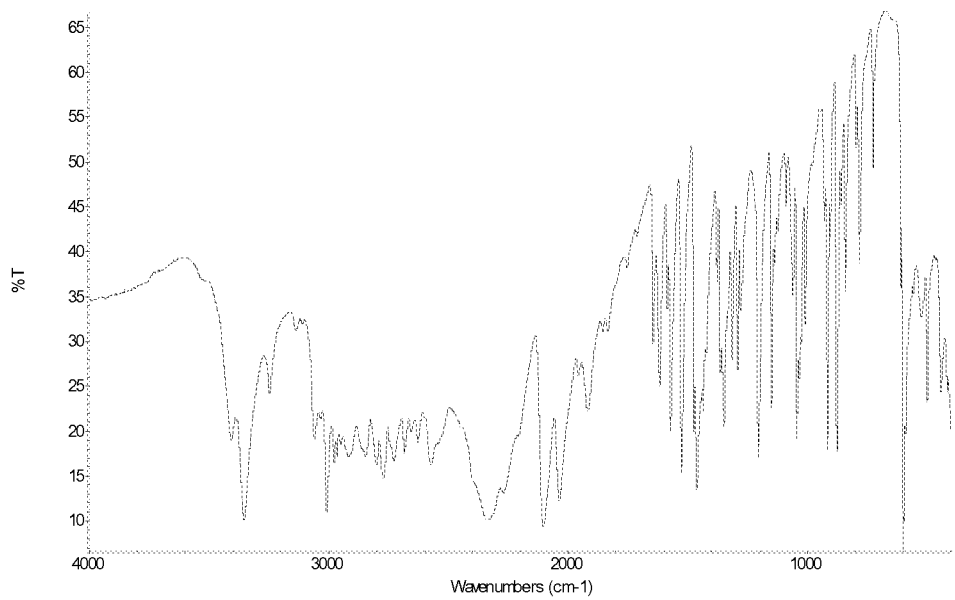
Figure 9 (IR Varenicline hydrochloride Form I)
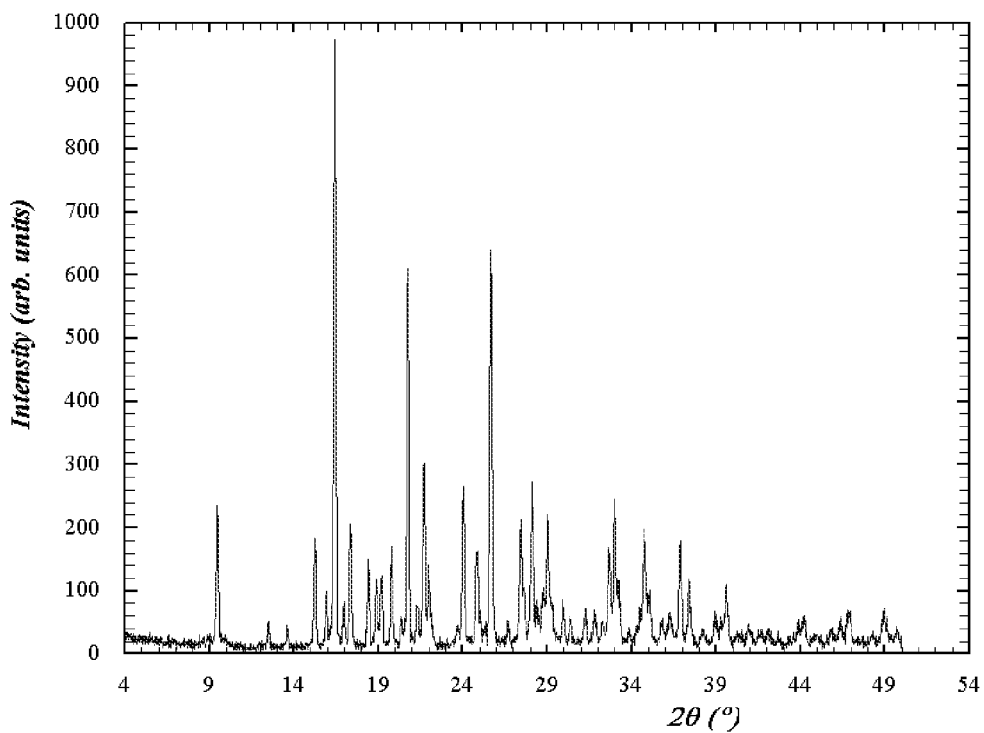
Figure 10 (XRD Varenicline hydrochloride Form I)

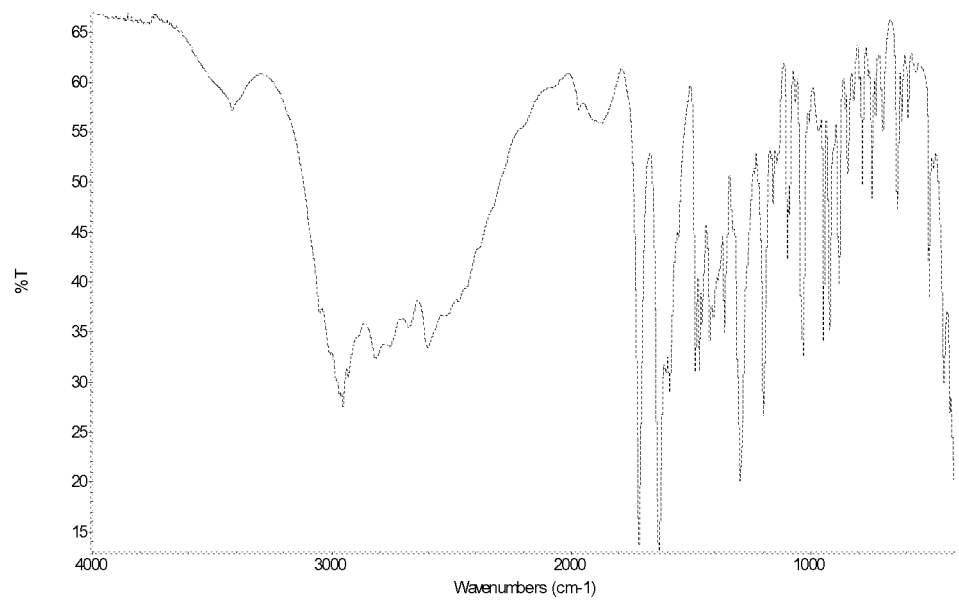
Figure 11 (IR Varenicline α-ketoglutarate Form I)
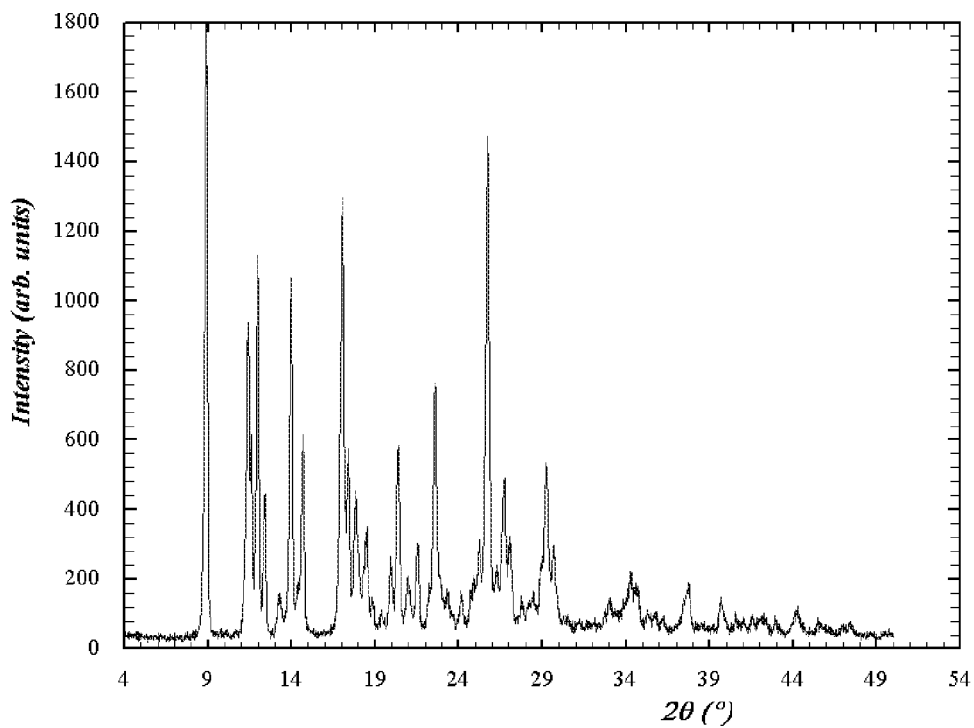
Figure 12 (XRD Varenicline α-ketoglutarate Form I)

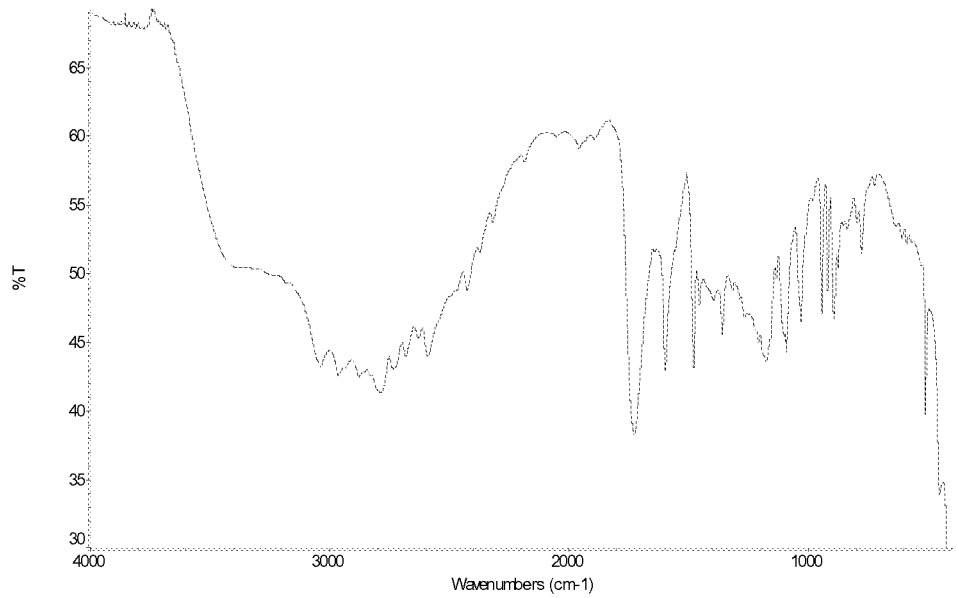
Figure 13 (IR Varenicline L-malate Form I)
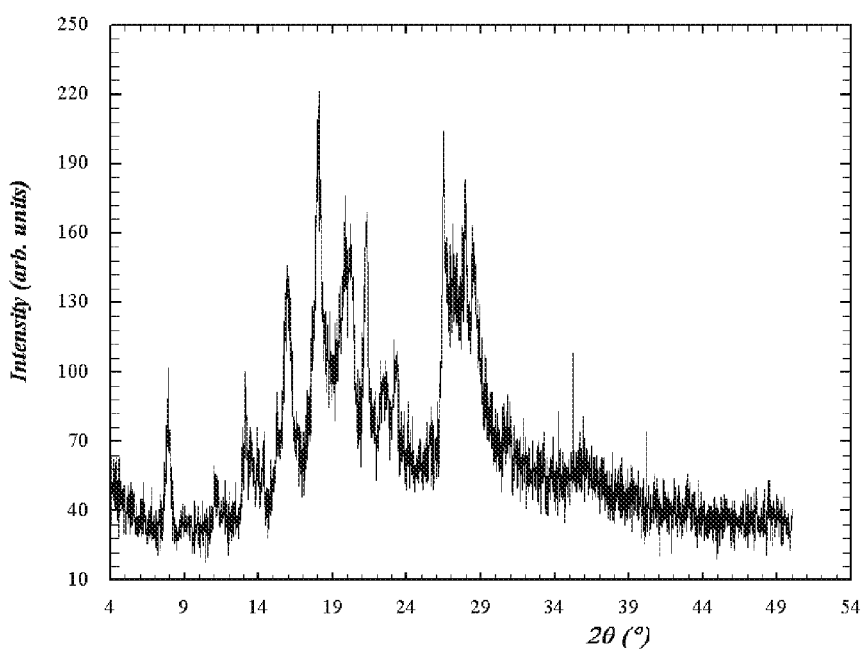
Figure 14 (XRD Varenicline L-malate Form I)

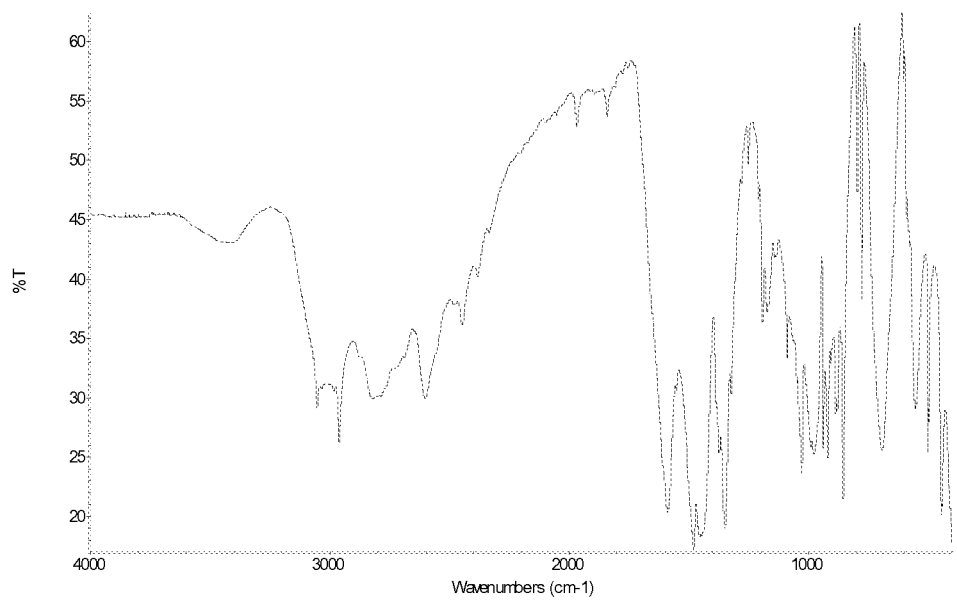
Figure 15 (IR Varenicline maleate Form I)
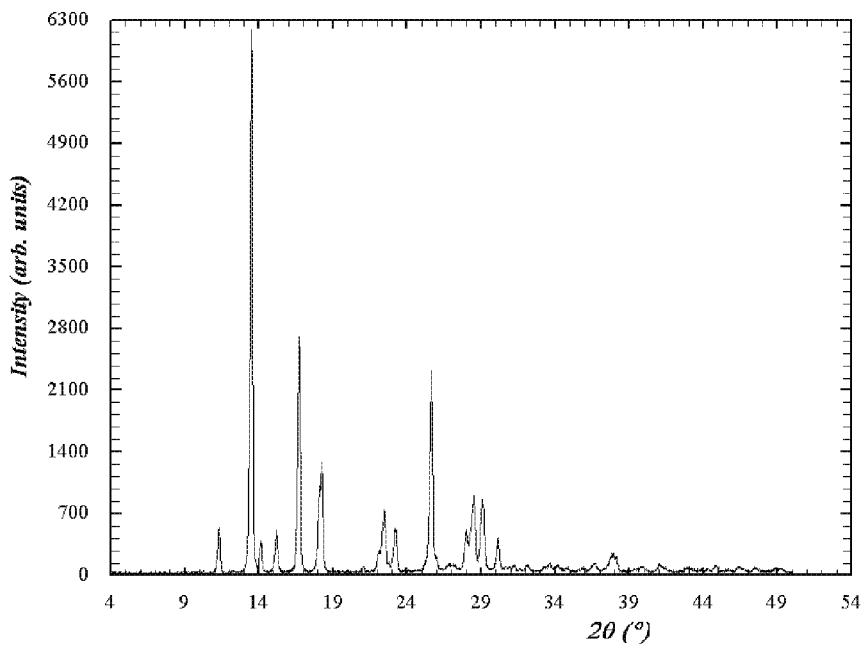
Figure 16 (XRD Varenicline maleate Form I)

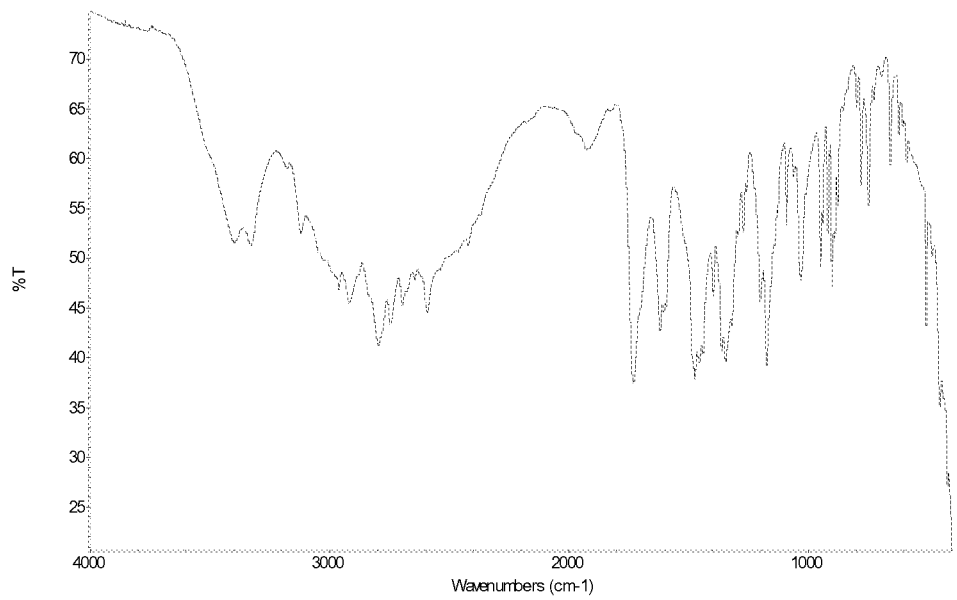
Figure 17 (IR Varenicline malonate Form I)
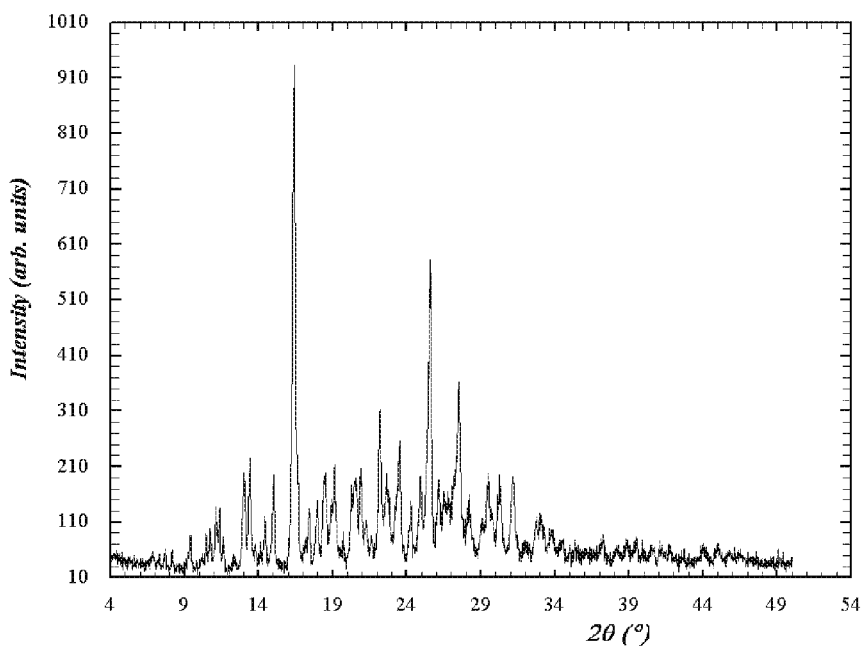
Figure 18 (XRD Varenicline malonate Form I)

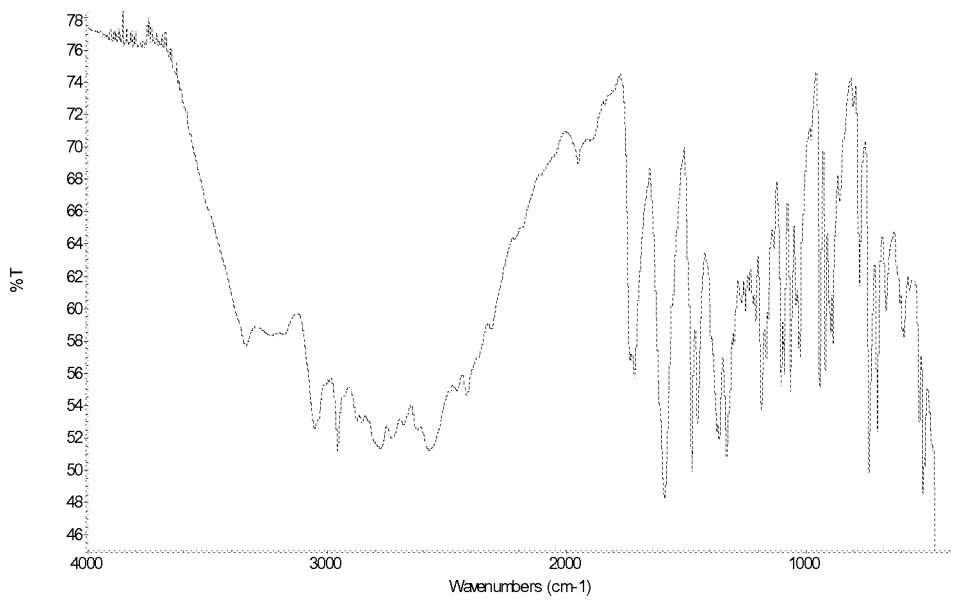
Figure 19 (IR Varenicline DL-mandelate Form I)
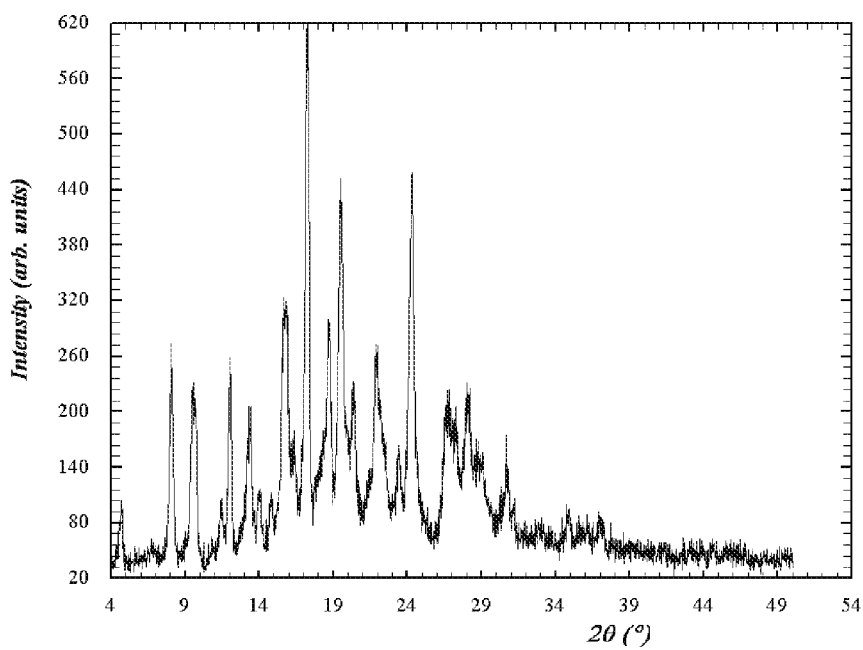
Figure 20 (XRD Varenicline DL-mandelate Form I)

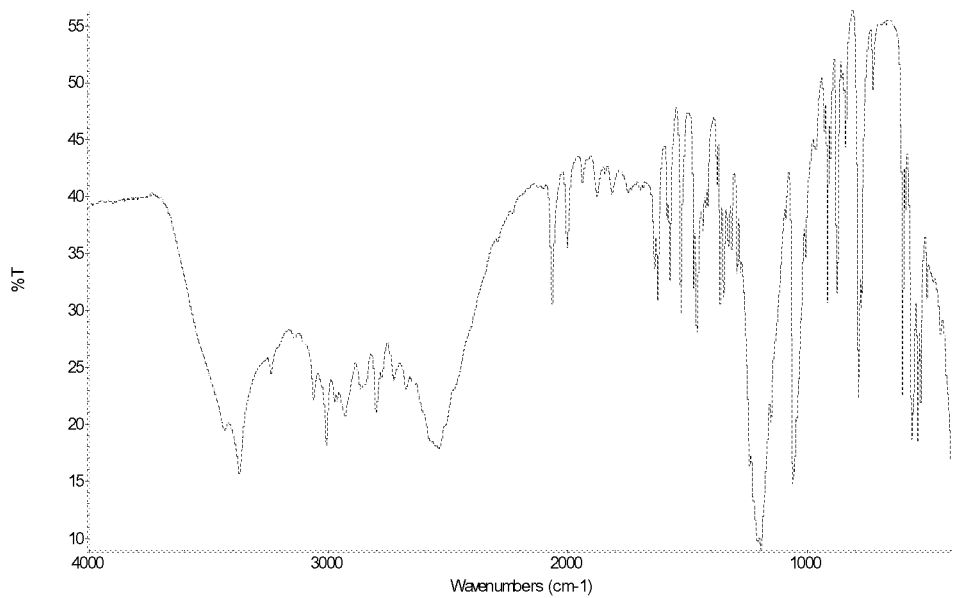
Figure 21 (IR Varenicline di-mesylate Form I)
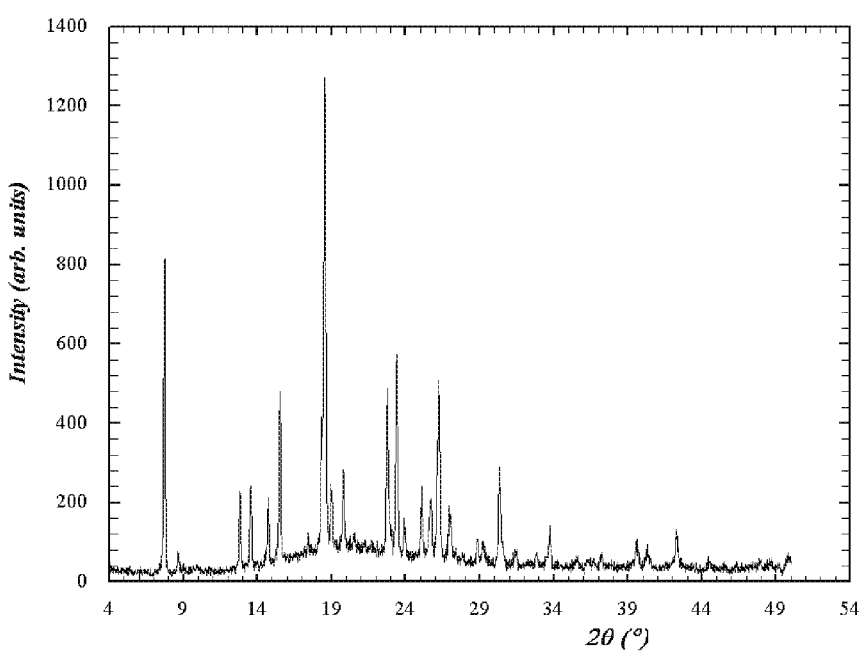
Figure 22 (XRD Varenicline di-mesylate Form I)

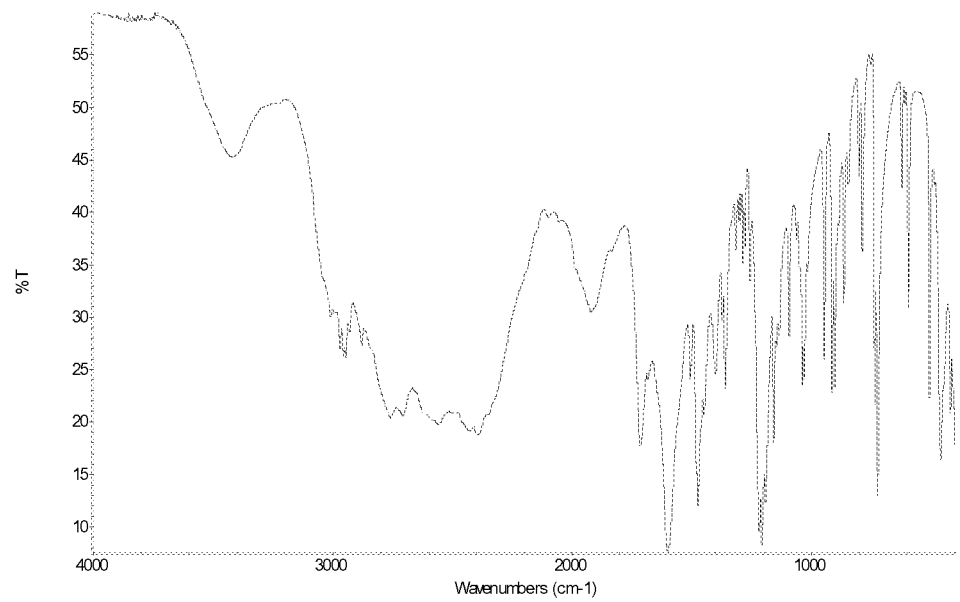
Figure 23 (IR Varenicline oxalate Form I)
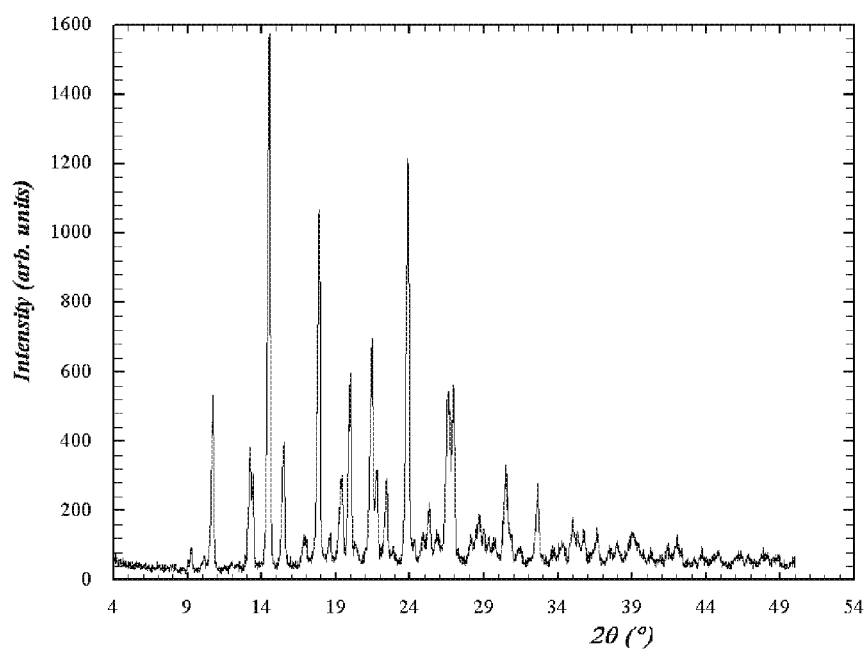
Figure 24 (XRD Varenicline oxalate Form I)

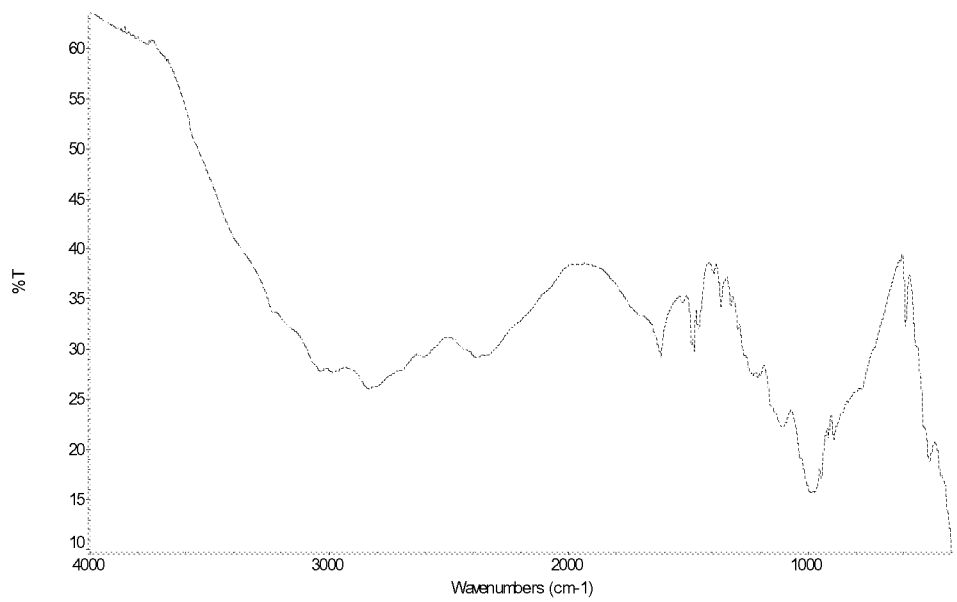
Figure 25 (IR Varenicline phosphate Form I)
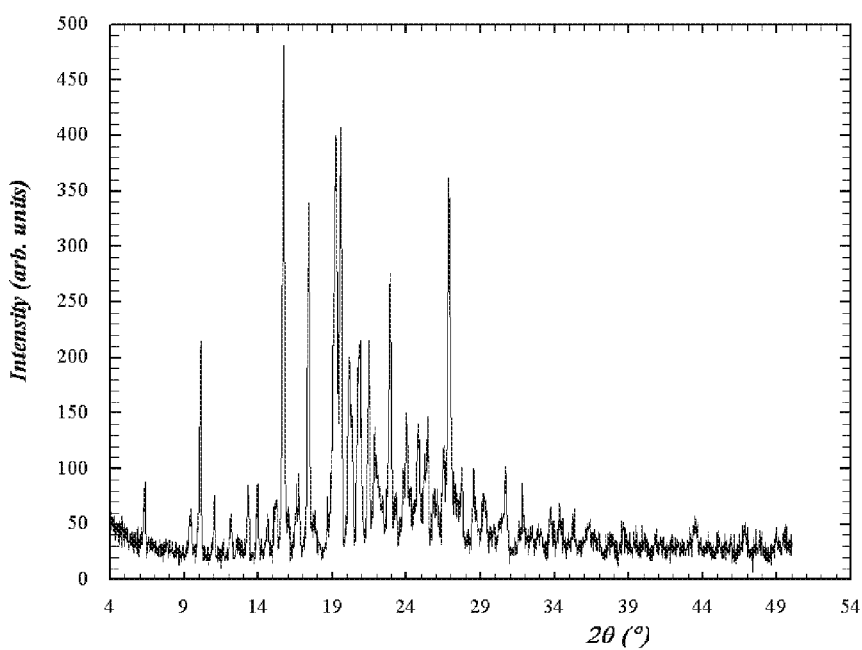
Figure 26 (XRD Varenicline phosphate Form I)

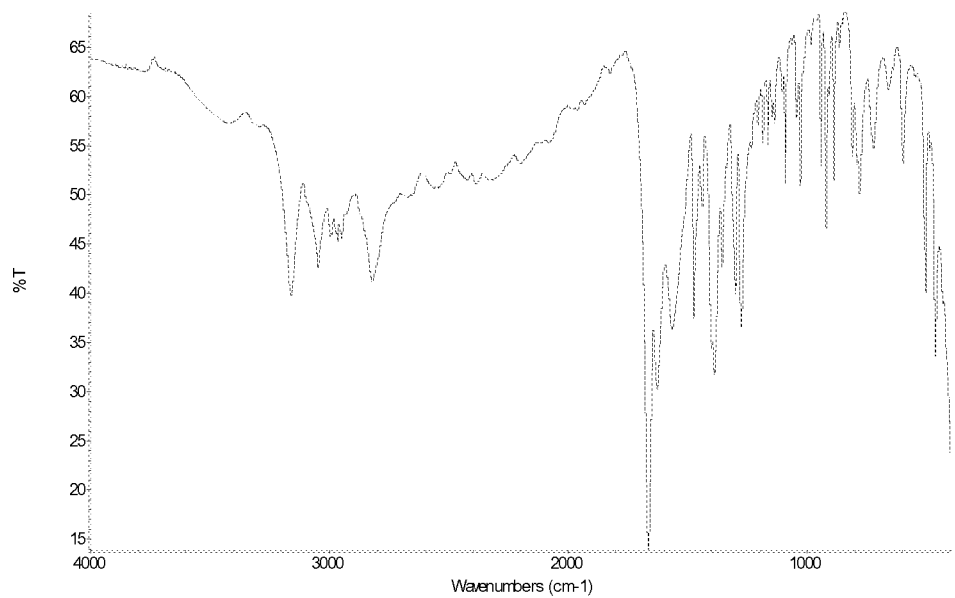
Figure 27 (IR Varenicline pyroglutamate Form I)
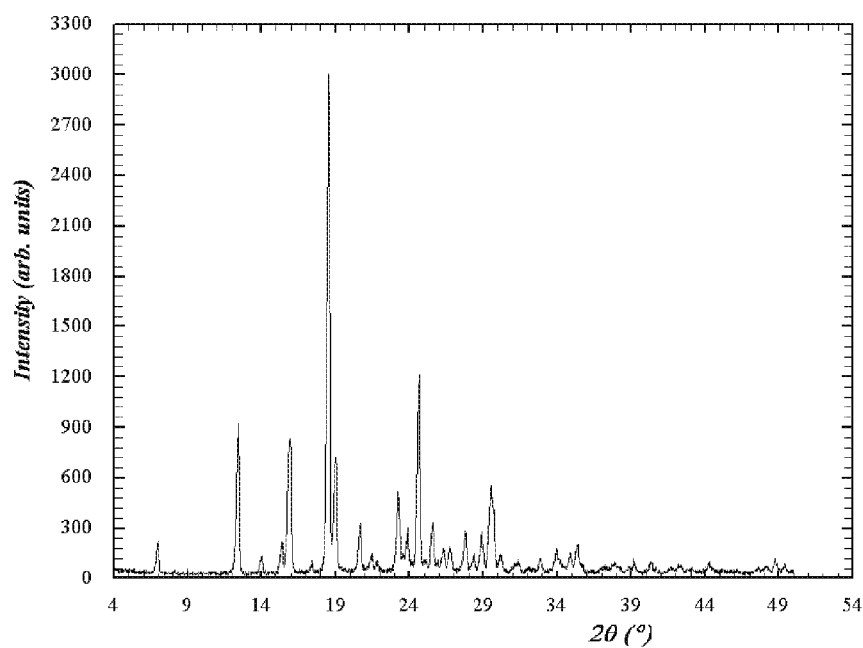
Figure 28 (XRD Varenicline pyroglutamate Form I)

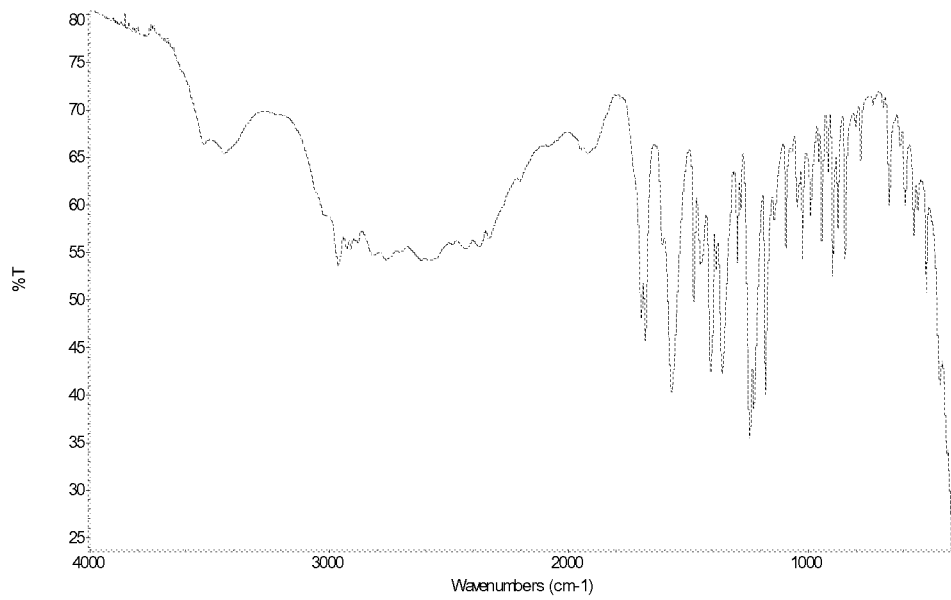
Figure 29 (IR Varenicline succinate Form I)
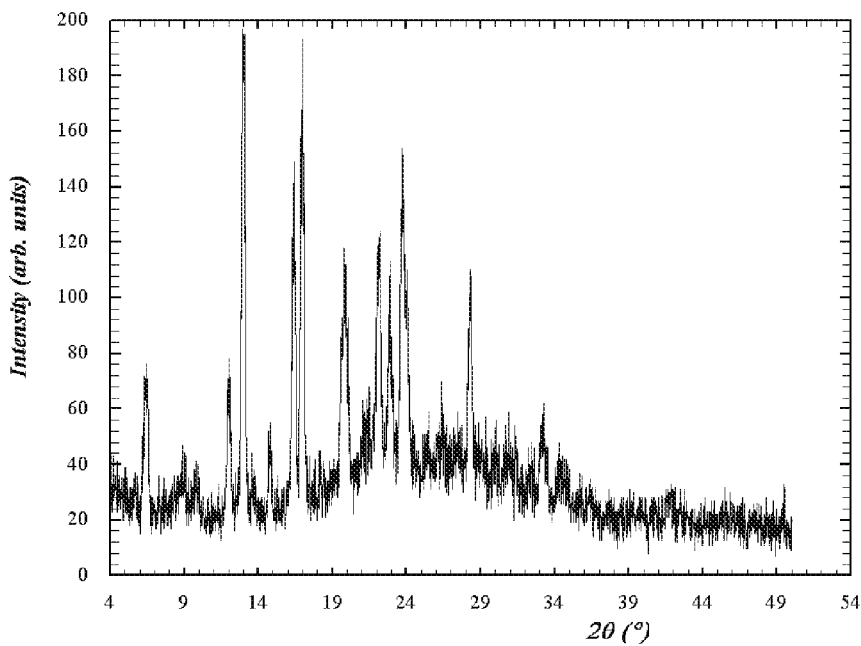
Figure 30 (XRD Varenicline succinate Form I)

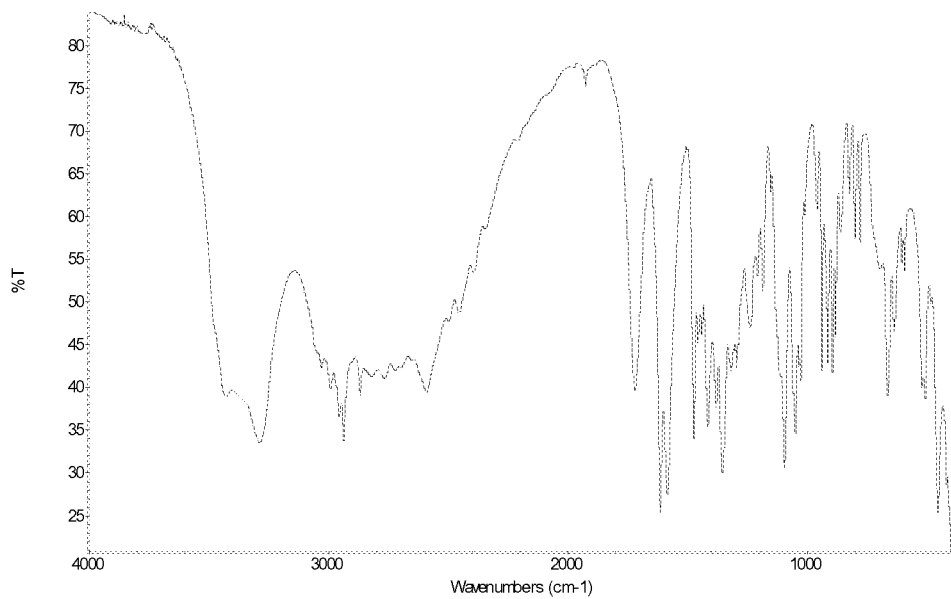
Figure 31 (IR Varenicline galactarate Form I)
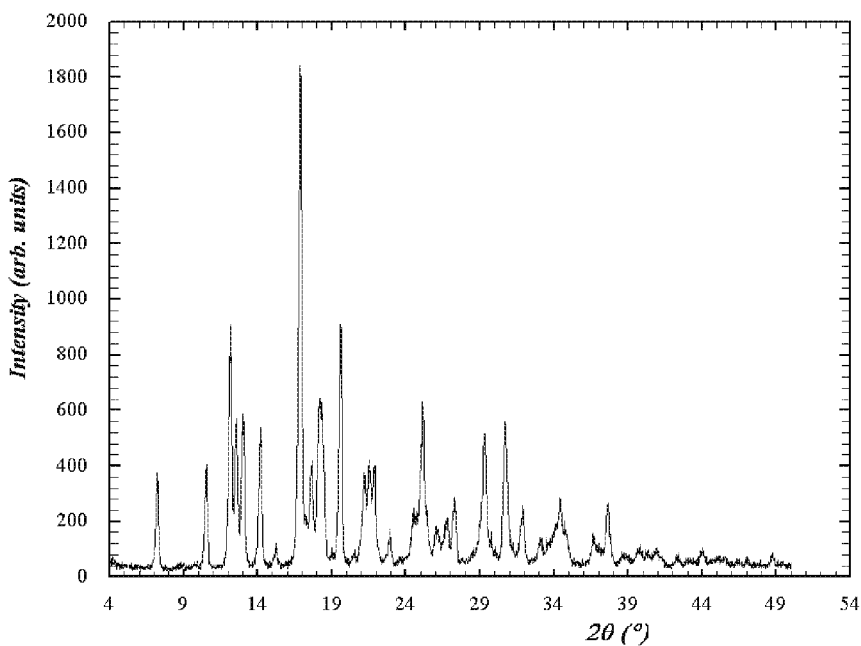
Figure 32 (XRD Varenicline galactarate Form I)

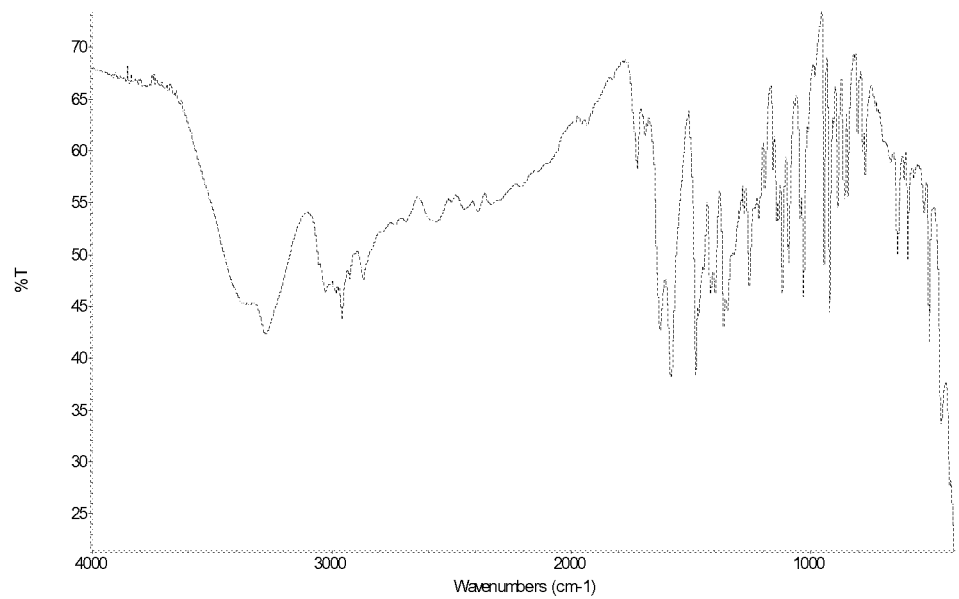
Figure 33 (IR Varenicline DL-lactate Form I)
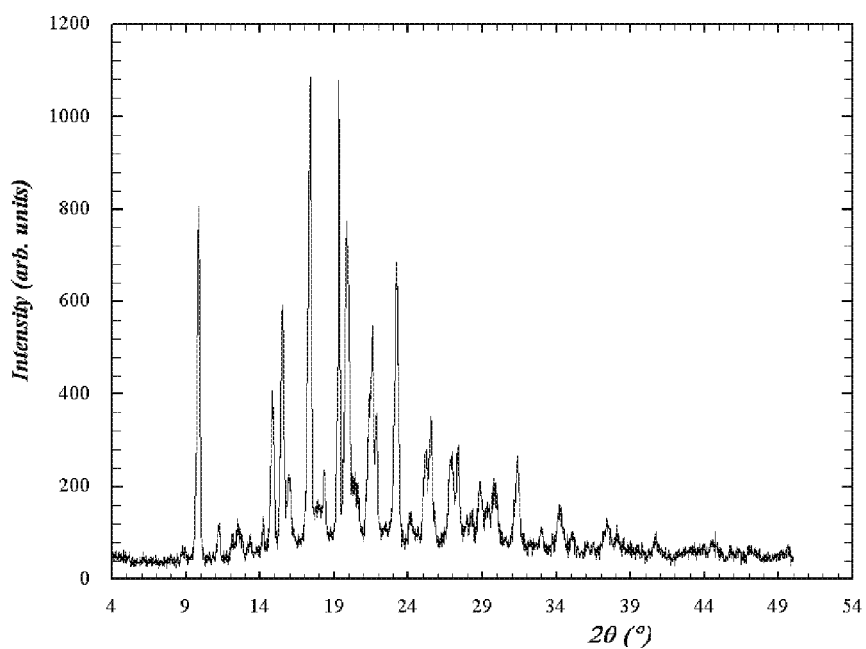
Figure 34 (XRD Varenicline DL-lactate Form I)

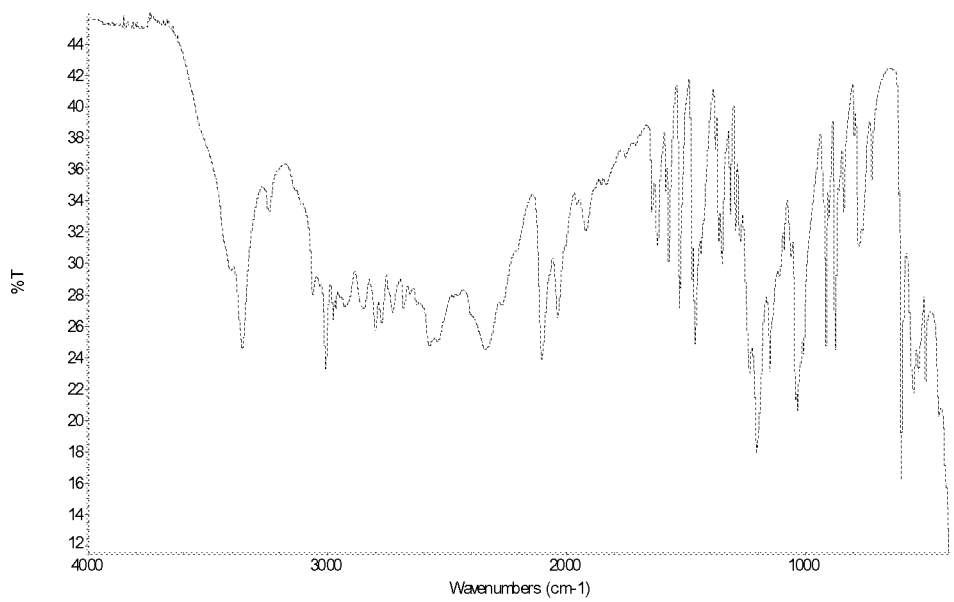
Figure 35 (IR Varenicline 1,2-ethane disulfonate Form I)
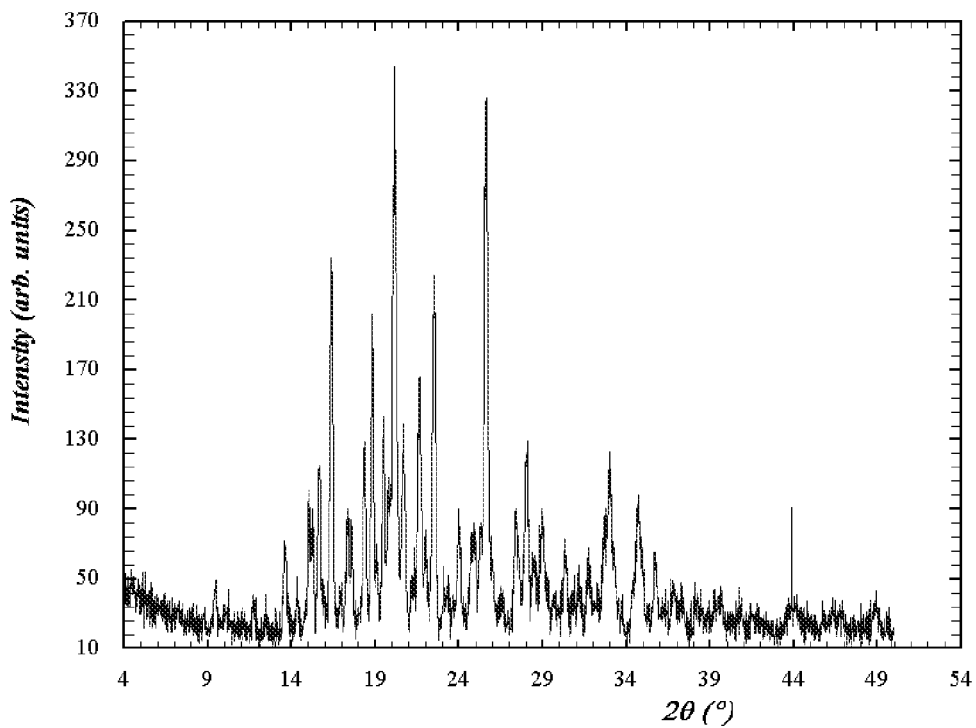
Figure 36 (XRD Varenicline 1,2-ethane disulfonate Form I)

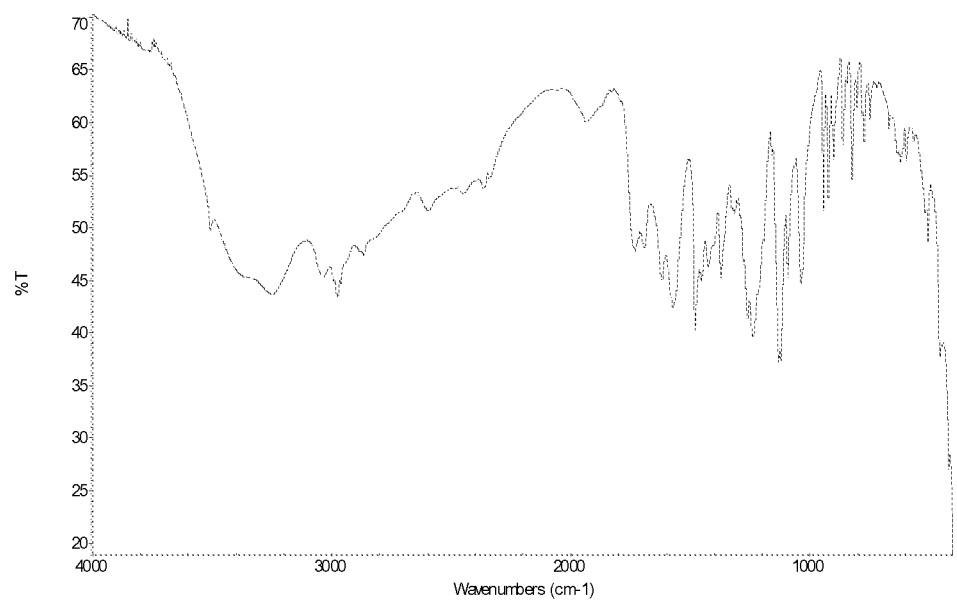
Figure 37 (IR Varenicline hemi-L-lactate Form I)
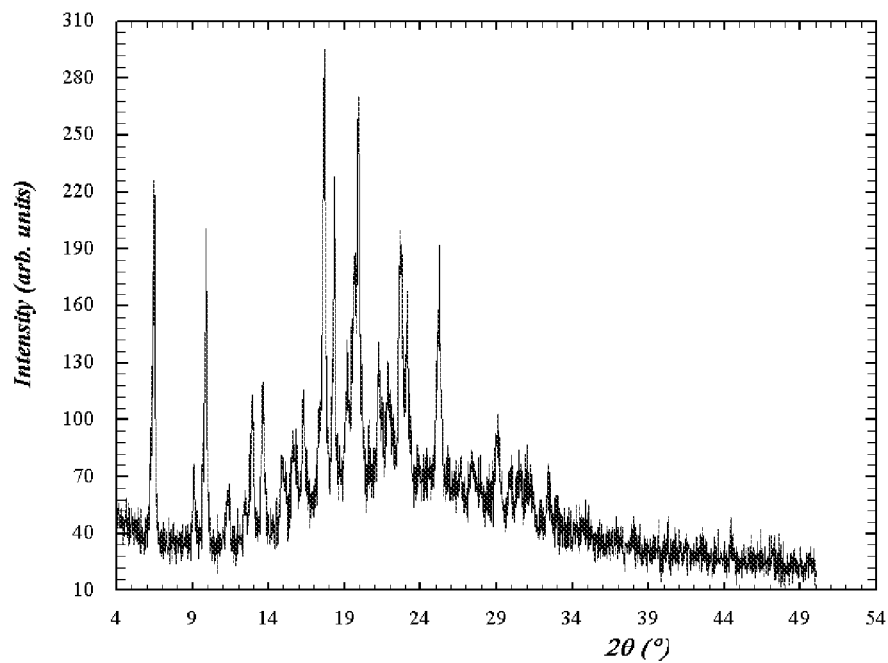
Figure 38 (XRD Varenicline hemi-L-lactate Form I)

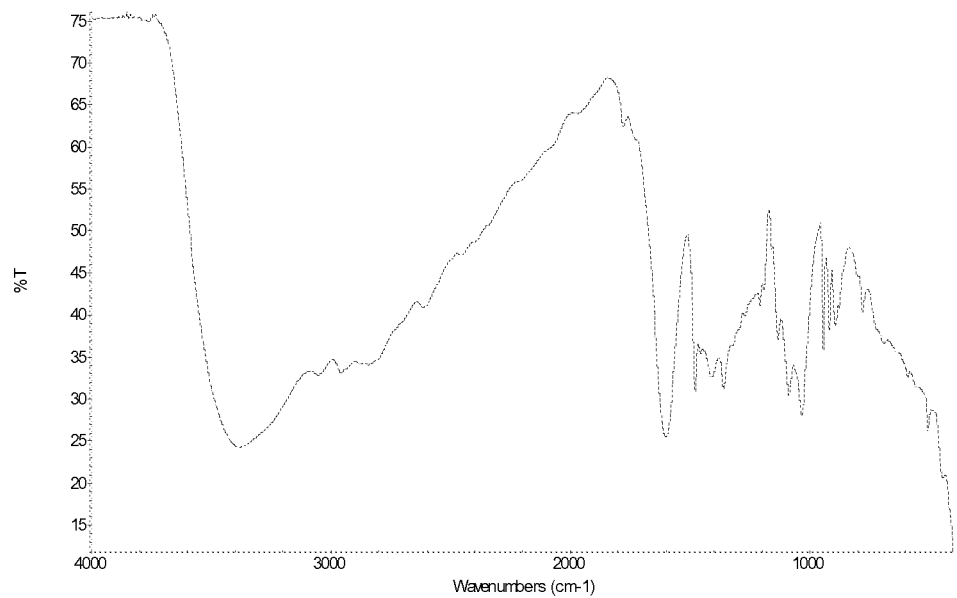
Figure 39 (IR Varenicline gluconate amorphous form)
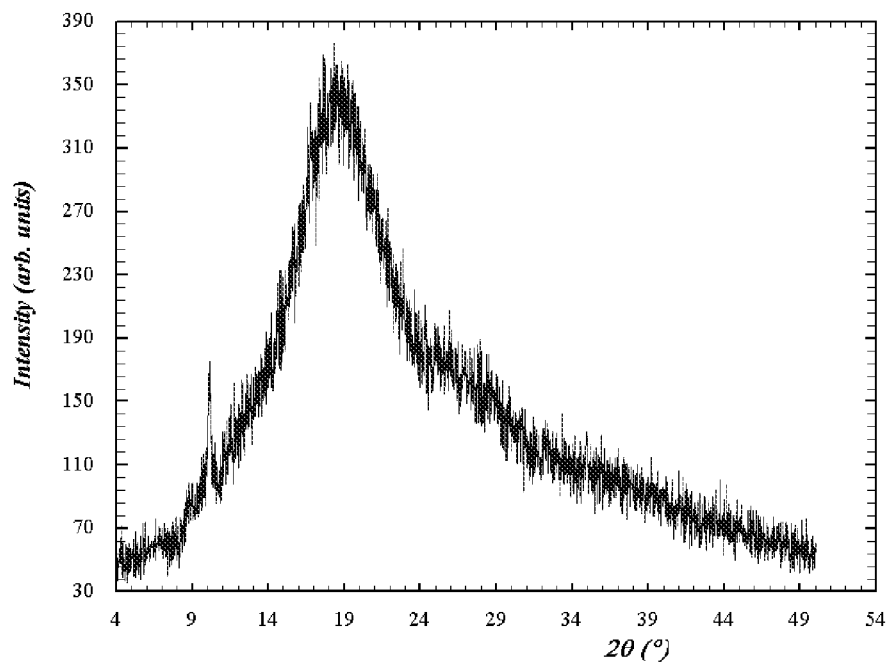
Figure 40 (XRD Varenicline Gluconate amorphous form)

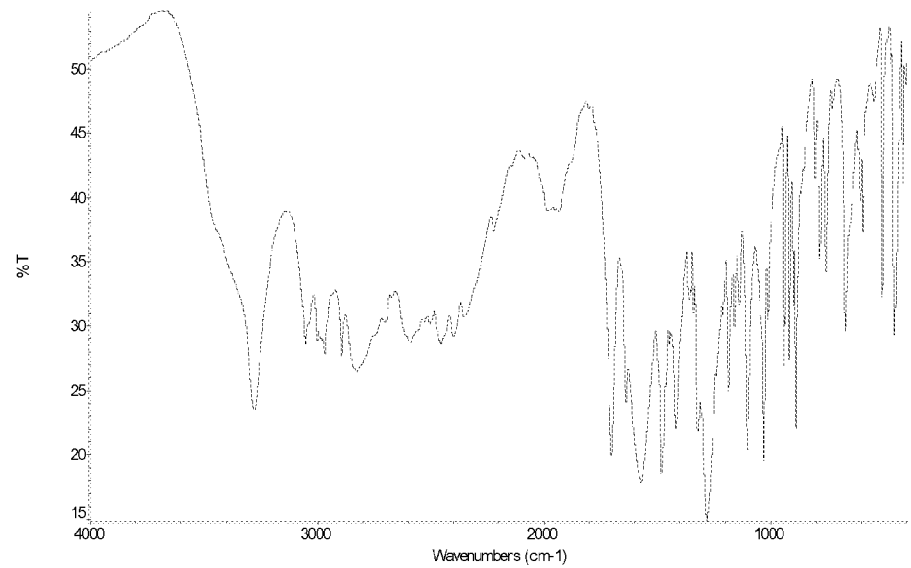
Figure 41 (IR Varenicline malate Form II)
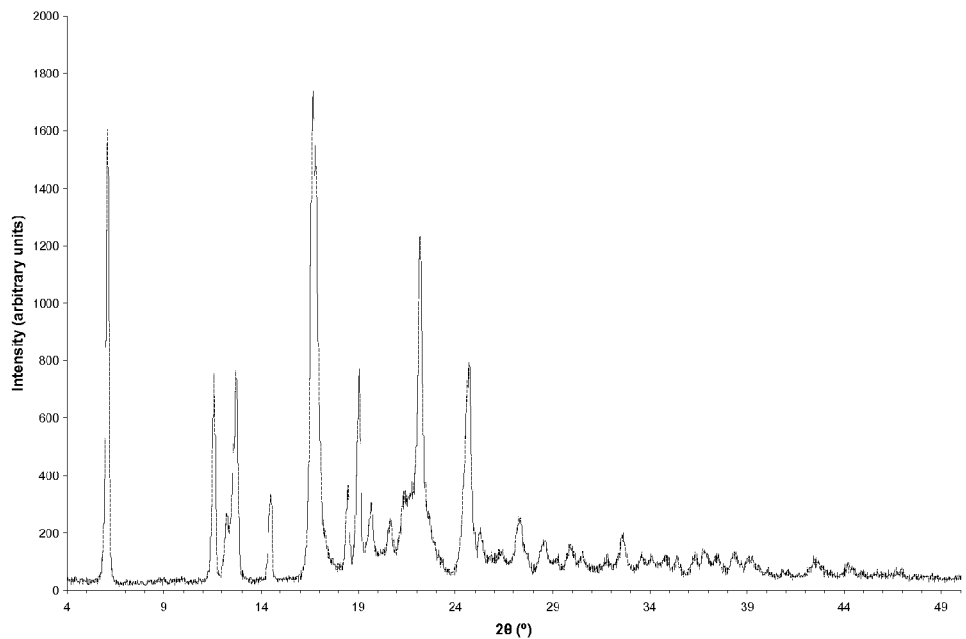
Figure 42 (XRD Varenicline malate Form II)

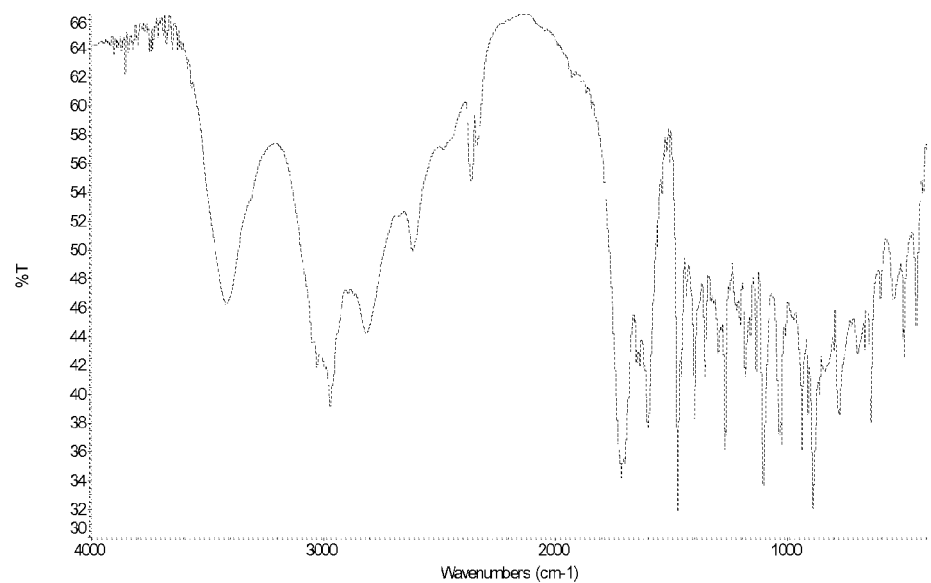
Figure 43 (IR Varenicline malate Form III)
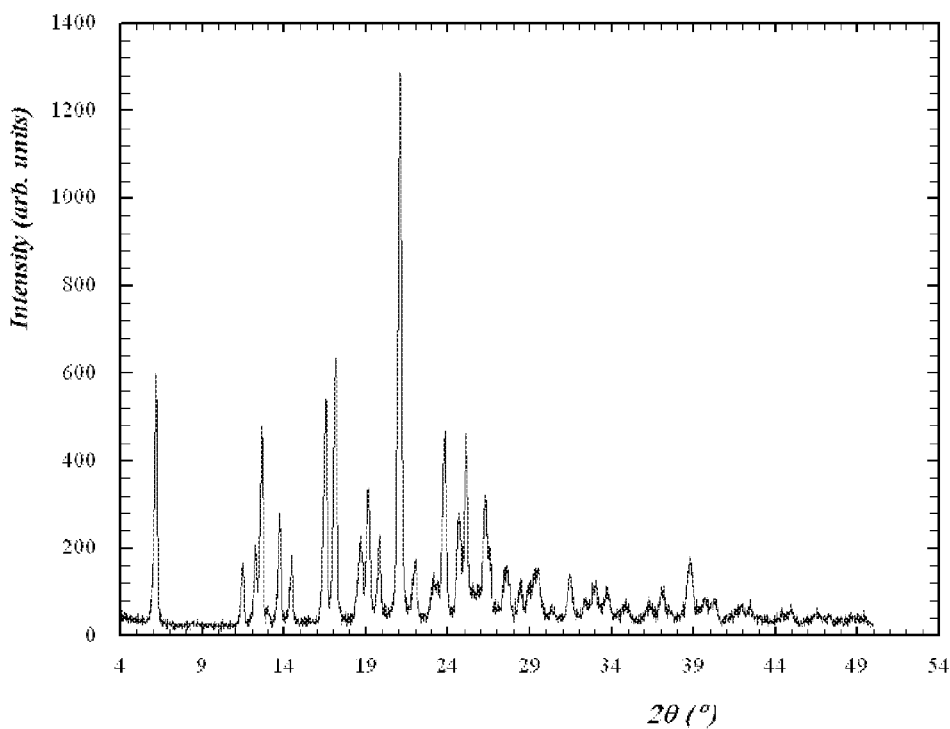
Figure 44 (XRD Varenicline malate Form III)

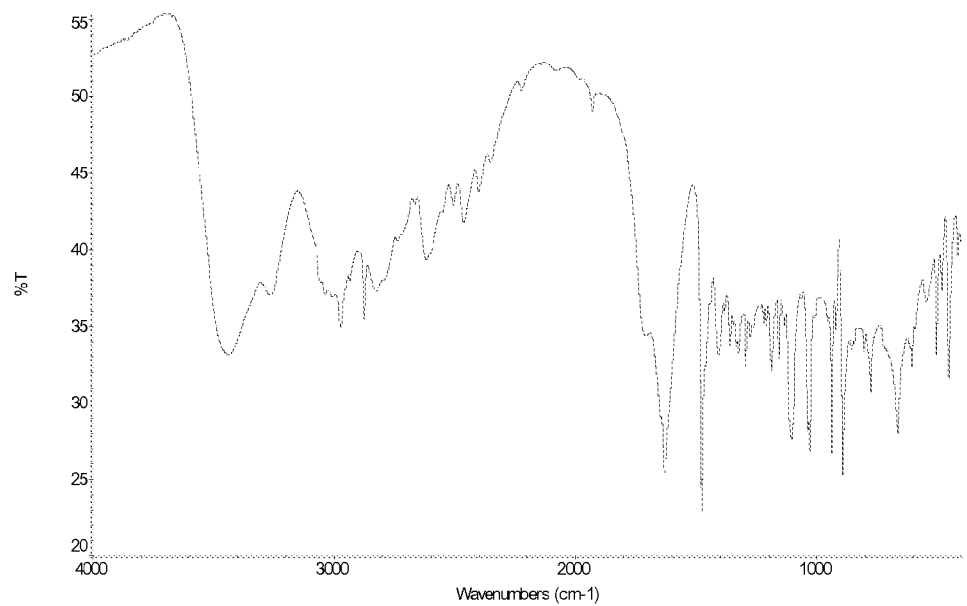
Figure 45 (IR Varenicline malate Form IV)
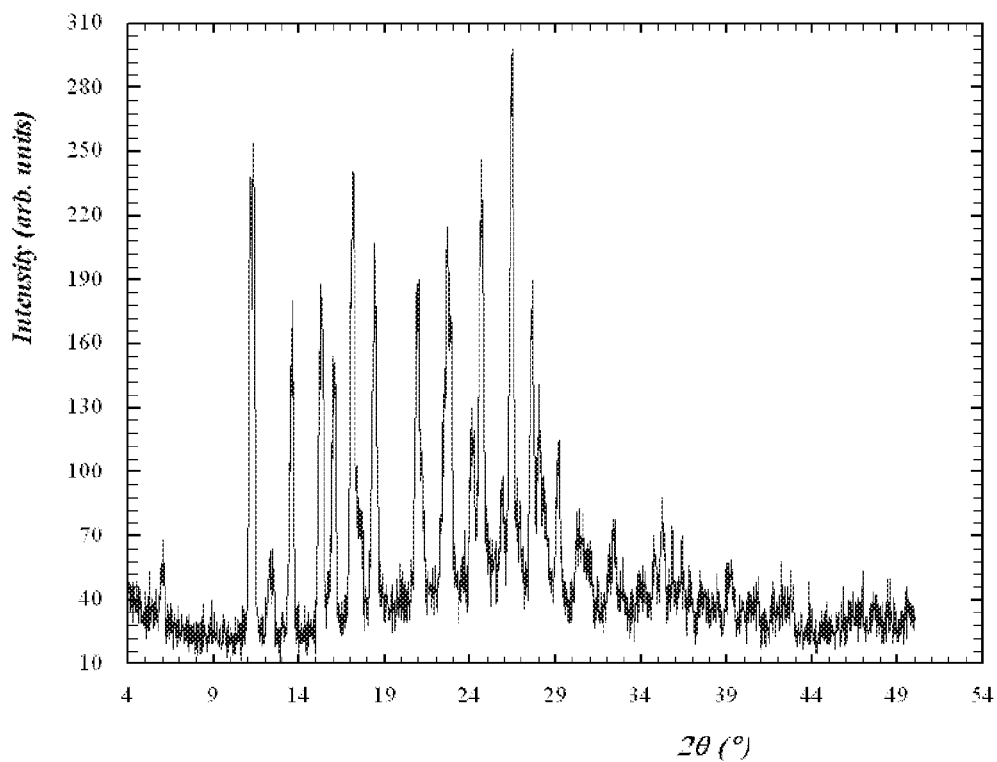
Figure 46 (XRD Varenicline malate Form IV)

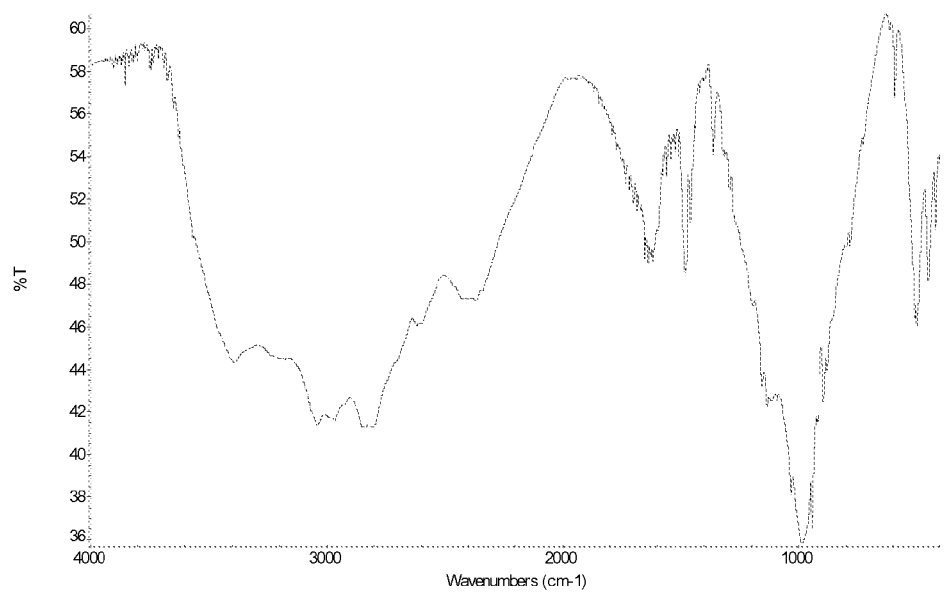
Figure 47 (IR Varenicline phosphate Form II)
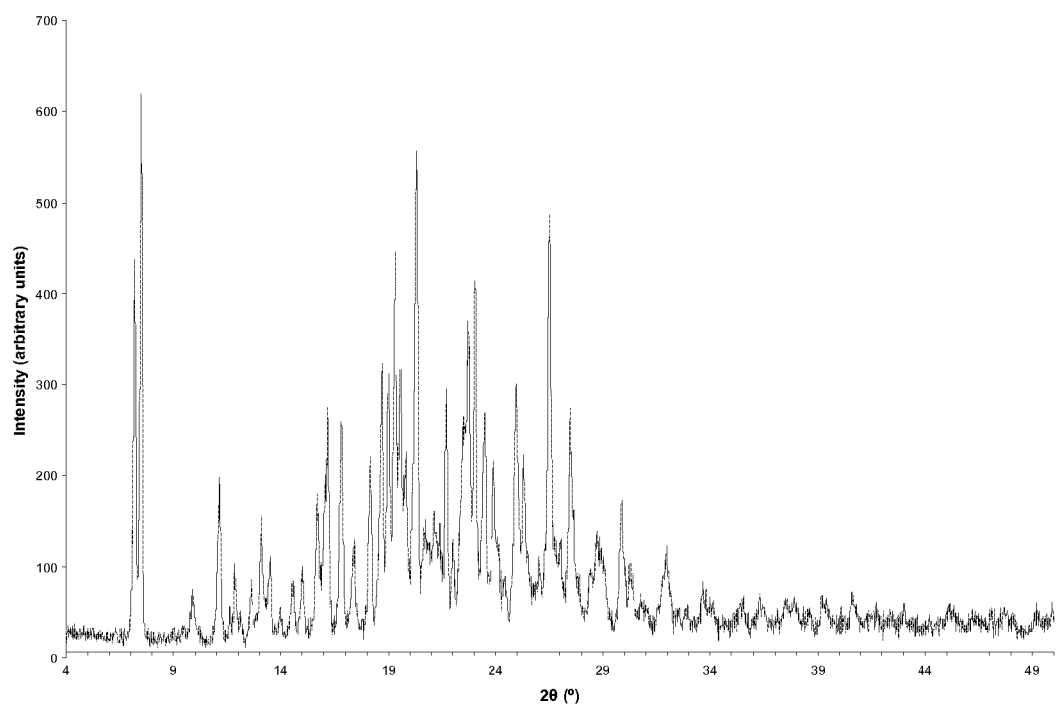
Figure 48 (XRD Varenicline phosphate Form II)

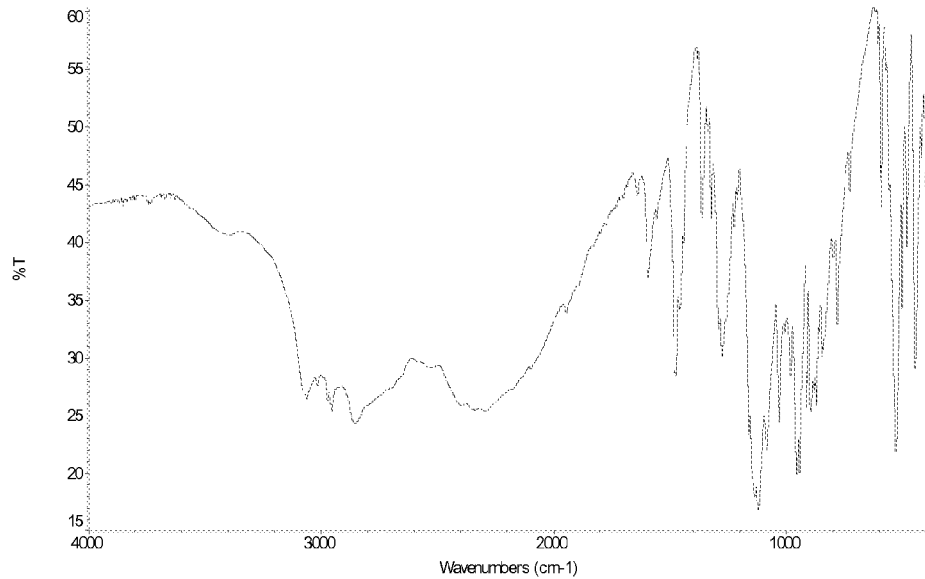
Figure 49 (IR Varenicline phosphate Form III)
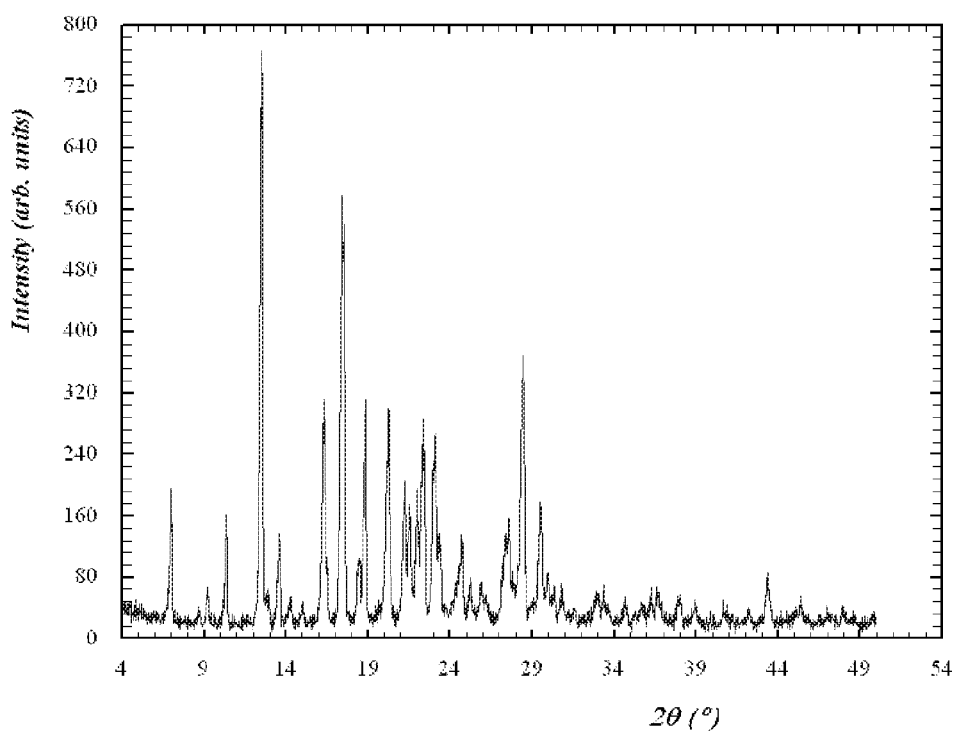
Figure 50 (XRD Varenicline phosphate Form III)

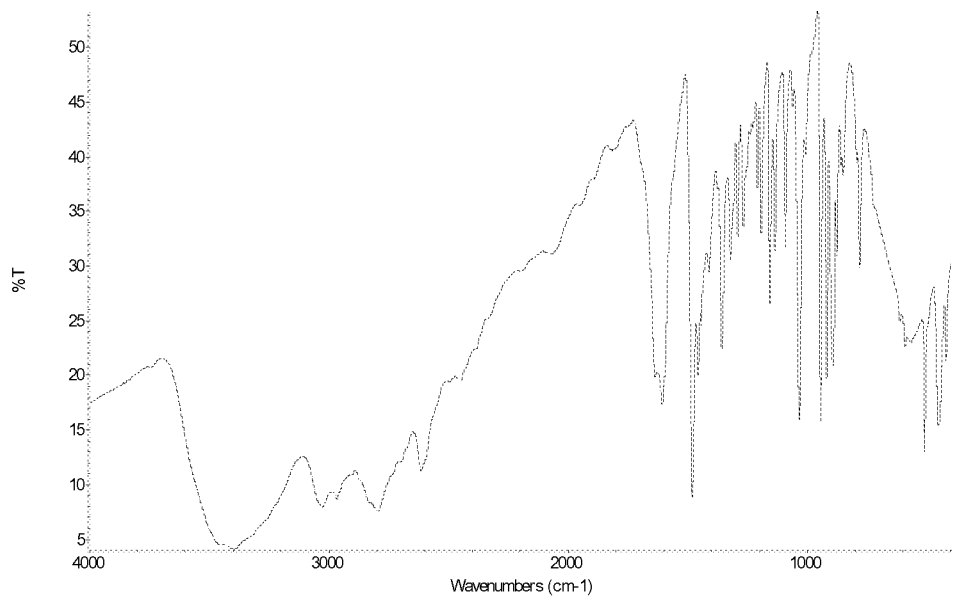
Figure 51 (IR Varenicline hydrochloride Form II)
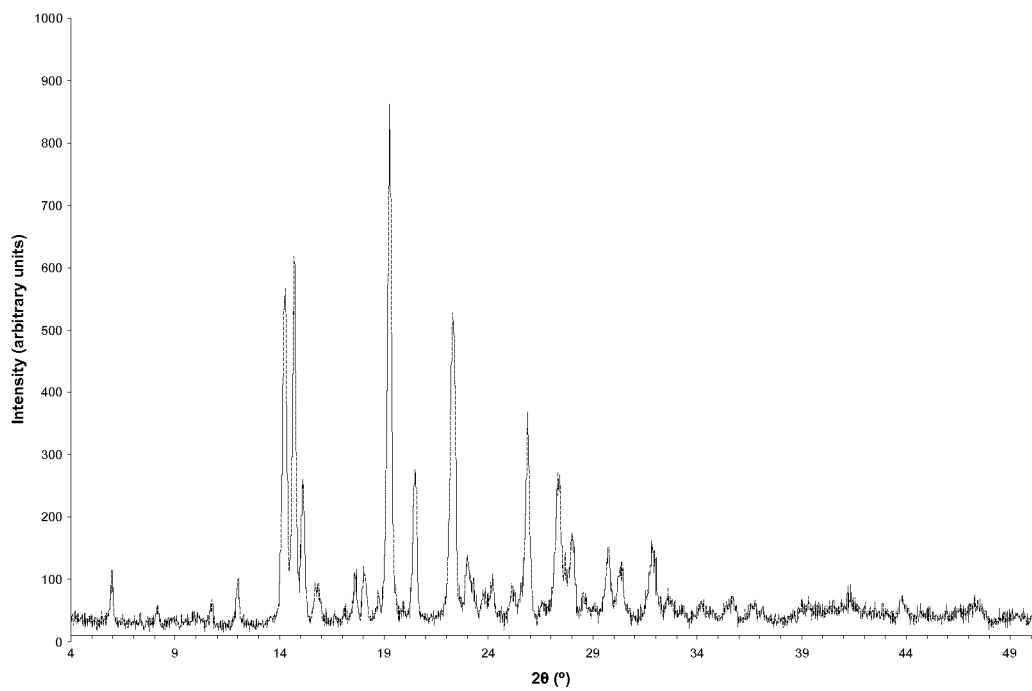
Figure 52 (XRD Varenicline hydrochloride Form II)

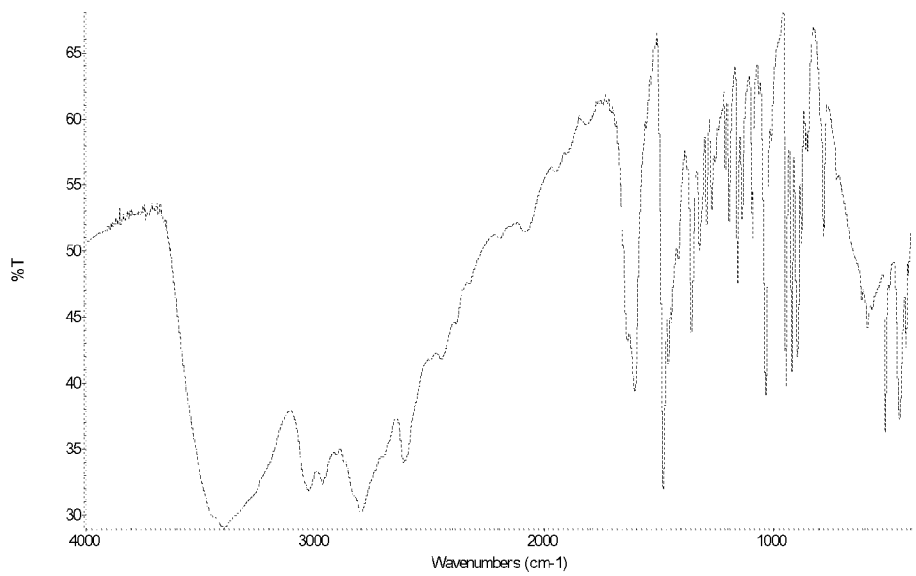
Figure 53 (IR Varenicline hydrochloride Form III)
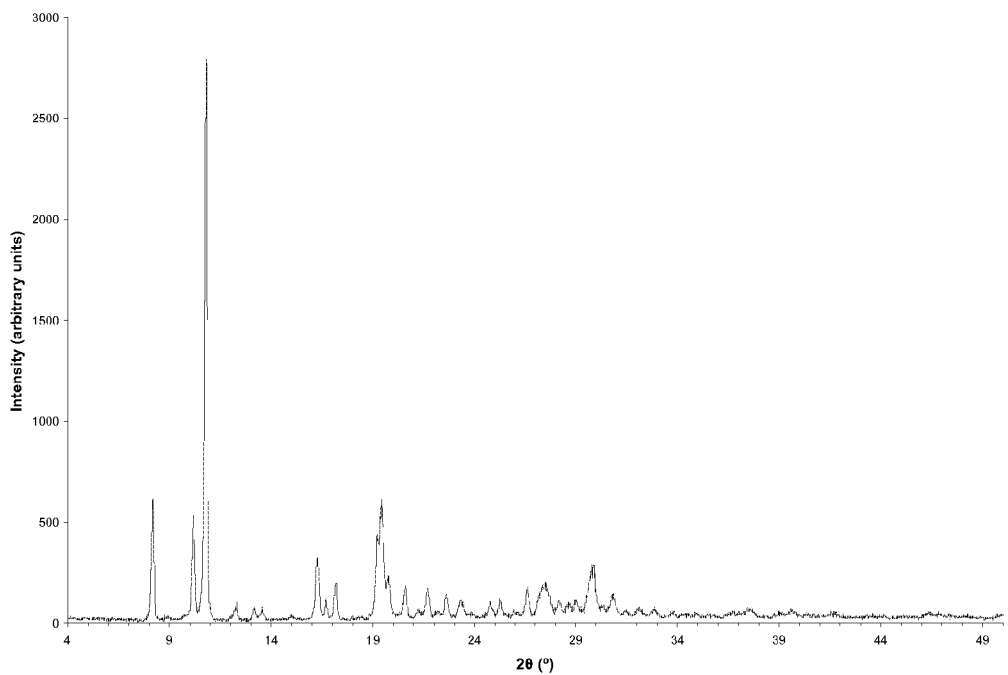
Figure 54 (XRD Varenicline hydrochloride Form III)

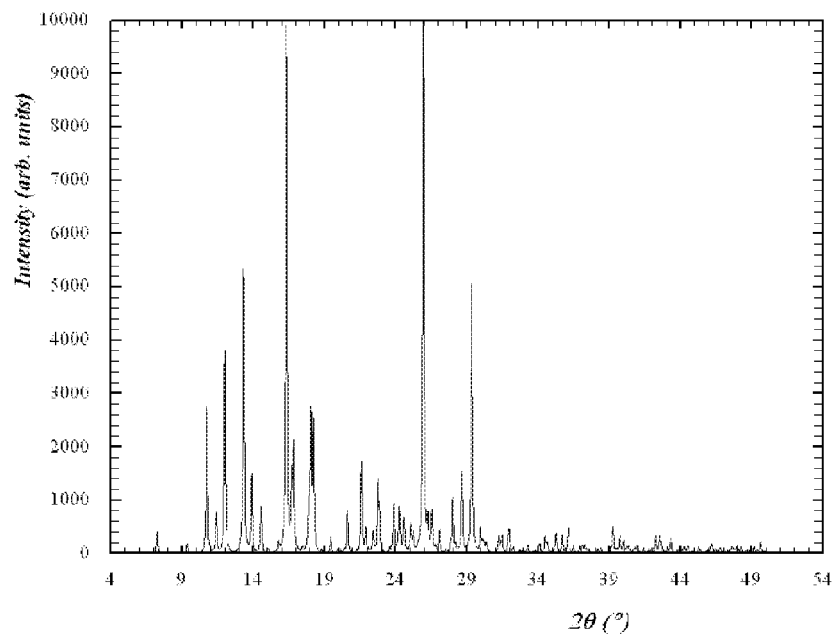
Figure 55 (simulated XR for single crystal of Varenicline fumarate Form I)
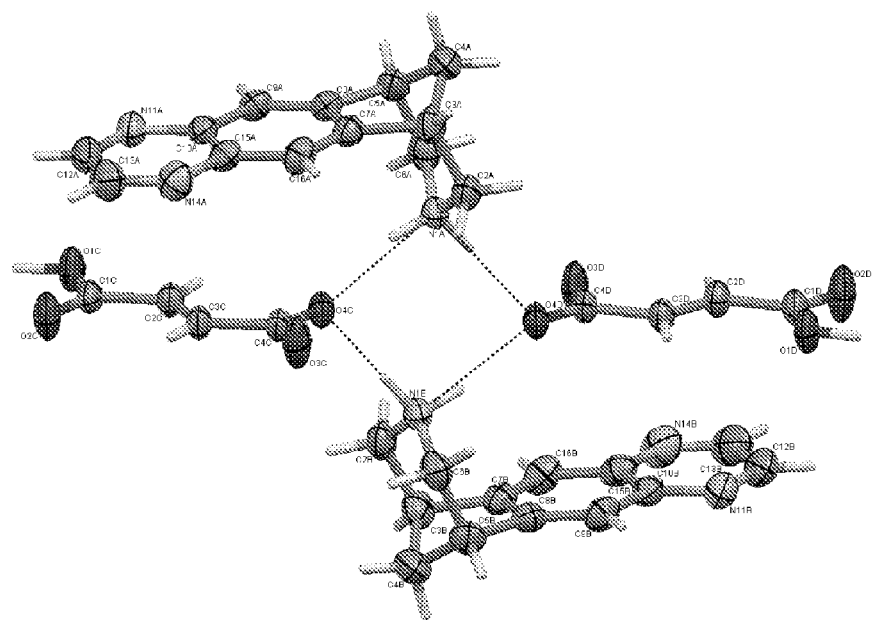
Figure 56 (Molecular structure of varenicline fumarate Form I with the atom-labelling scheme)

FUMARIC ACID SALT OF VARENICLINE

PRIORITY CLAIM

This is a U.S. national stage of PCT Application No. PCT/EP2009/052654, filed on Mar. 6, 2009, which claims priority of U.S. Provisional Patent Application Nos. 61/123,382, filed Apr. 8, 2008, and 61/068,384, filed Mar. 6, 2008, the contents of both of which are incorporated herein by reference.

FIELD OF THE INVENTION

The present invention relates to novel salt forms of varenicline base, to processes for their preparation and isolation, and to pharmaceutical compositions comprising the same.

BACKGROUND OF THE INVENTION

Varenicline (Compound I) is the international commonly accepted name for 7,8,9,10-tetrahydro-6,10-methano-6H-pyrazino[2,3-h][3]benzazepine (which is also known as 5,8,14-triazatetracyclo[10.3.1.0$^{2,11}$.0$^{4,9}$]-hexadeca-2(11),3,5,7,9-pentaene), and has an empirical formula of $C_{13}H_{13}N_3$ and a molecular weight of 211.27. Varenicline L-tartrate is a commercially marketed pharmaceutically active substance known to be useful for the treatment of smoking addiction.

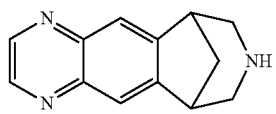

(I)

Varenicline L-tartrate is a partial agonist selective for $\alpha_4\beta_2$ nicotinic acetylcholine receptor subtypes. In the United States, varenicline L-tartrate is marketed under the name Chantix™ for the treatment of smoking cessation.

Varenicline base and its pharmaceutically acceptable acid addition salts are described in U.S. Pat. No. 6,410,550. In particular, Example 26 of U.S. Pat. No. 6,410,550 describes the preparation of varenicline base and its hydrochloride salt using 1-(4,5-dinitro-10-aza-tricyclo[6.3.1.0$^{2,7}$]dodeca-2,4,6-trien-10-yl)-2,2,2-trifluoroethanone as starting compound. In particular, the hydrochloride salt of varenicline described in this reference has been obtained after crystallization from methanol/diethyl ether (The present inventors have reproduced said crystallization, and the varenicline hydrochloride obtained has been denominated herein as Form II. See Comparative Example 1). In addition, Examples 1 and 2 of U.S. Pat. No. 6,787,549B2 describe the preparation of varenicline citrate in different forms (Forms A and B). Also, Examples 1 and 2 of U.S. Pat. No. 6,794,388B2 describe the preparation of varenicline succinate in different forms (i.e. an anhydrous form and a hydrate form). Further, Examples 1 to 4 of U.S. Pat. No. 6,890,927B2 describe the preparation of varenicline tartrate in different forms (Forms A, B, and C).

Different salt forms of the same pharmaceutically active moiety differ in their physical properties such as melting point, solubility, chemical reactivity, etc. These properties may appreciably influence pharmaceutical properties such as dissolution rate and bioavailability.

In addition, polymorphism, which is defined as the ability of a substance to crystallize in more than one crystal lattice arrangement, can also influence many aspects of solid state properties of a drug. Different crystal modifications of a substance may differ considerably from one another in many respects such as their solubility, dissolution rate and finally bioavailability.

There exists a need for salt forms, which in addition might be in crystalline form, of such material that have superior chemical and/or physical properties that are useful in drug delivery applications.

This application sets forth several novel salt forms of varenicline base. These salt forms have been prepared and characterized as described herein.

BRIEF DESCRIPTION OF THE FIGURES

FIG. 1 illustrates the Infrared (IR) spectra of varenicline hemi-adipate Form I obtained in Example 1.

FIG. 2 illustrates the X-ray powder diffractogram (XRD) of varenicline hemi-adipate Form I obtained in Example 1.

FIG. 3 illustrates the Infrared (IR) spectra of varenicline fumarate Form I obtained in Example 2.

FIG. 4 illustrates the X-ray powder diffractogram (XRD) of varenicline fumarate Form I obtained in Example 2.

FIG. 5 illustrates the Infrared (IR) spectra of varenicline glutarate Form I obtained in Example 3.

FIG. 6 illustrates the X-ray powder diffractogram (XRD) of varenicline glutarate Form I obtained in Example 3.

FIG. 7 illustrates the Infrared (IR) spectra of varenicline glycolate Form I obtained in Example 4.

FIG. 8 illustrates the X-ray powder diffractogram (XRD) of varenicline glycolate Form I obtained in Example 4.

FIG. 9 illustrates the Infrared (IR) spectra of varenicline hydrochloride Form I obtained in Example 5.

FIG. 10 illustrates the X-ray powder diffractogram (XRD) of varenicline hydrochloride Form I obtained in Example 5.

FIG. 11 illustrates the Infrared (IR) spectra of varenicline α-ketoglutarate Form I obtained in Example 6.

FIG. 12 illustrates the X-ray powder diffractogram (XRD) of varenicline α-ketoglutarate Form I obtained in Example 6.

FIG. 13 illustrates the Infrared (IR) spectra of varenicline L-malate Form I obtained in Example 7.

FIG. 14 illustrates the X-ray powder diffractogram (XRD) of varenicline L-malate Form I obtained in Example 7.

FIG. 15 illustrates the Infrared (IR) spectra of varenicline maleate Form I obtained in Example 8.

FIG. 16 illustrates the X-ray powder diffractogram (XRD) of varenicline maleate Form I obtained in Example 8.

FIG. 17 illustrates the Infrared (IR) spectra of varenicline malonate Form I obtained in Example 9.

FIG. 18 illustrates the X-ray powder diffractogram (XRD) of varenicline malonate Form I obtained in Example 9.

FIG. 19 illustrates the Infrared (IR) spectra of varenicline DL-mandelate Form I obtained in Example 10.

FIG. 20 illustrates the X-ray powder diffractogram (XRD) of varenicline DL-mandelate Form I obtained in Example 10.

FIG. 21 illustrates the Infrared (IR) spectra of varenicline di-mesylate Form I obtained in Example 11.

FIG. 22 illustrates the X-ray powder diffractogram (XRD) of varenicline di-mesylate Form I obtained in Example 11.

FIG. 23 illustrates the Infrared (IR) spectra of varenicline oxalate Form I obtained in Example 12.

FIG. 24 illustrates the X-ray powder diffractogram (XRD) of varenicline oxalate Form I obtained in Example 12.

FIG. 25 illustrates the Infrared (IR) spectra of varenicline phosphate Form I obtained in Example 13.

FIG. 26 illustrates the X-ray powder diffractogram (XRD) of varenicline phosphate Form I obtained in Example 13.

FIG. 27 illustrates the Infrared (IR) spectra of varenicline pyroglutamate Form I obtained in Example 14.

FIG. 28 illustrates the X-ray powder diffractogram (XRD) of varenicline pyroglutamate Form I obtained in Example 14.

FIG. 29 illustrates the Infrared (IR) spectra of varenicline succinate Form I obtained in Example 15.

FIG. 30 illustrates the X-ray powder diffractogram (XRD) of varenicline succinate Form I obtained in Example 15.

FIG. 31 illustrates the Infrared (IR) spectra of varenicline galactarate Form I obtained in Example 16.

FIG. 32 illustrates the X-ray powder diffractogram (XRD) of varenicline galactarate Form I obtained in Example 16.

FIG. 33 illustrates the Infrared (IR) spectra of varenicline DL-lactate Form I obtained in Example 17.

FIG. 34 illustrates the X-ray powder diffractogram (XRD) of varenicline DL-lactate Form I obtained in Example 17.

FIG. 35 illustrates the Infrared (IR) spectra of varenicline hemi-1,2-ethane disulfonate Form I obtained in Example 18.

FIG. 36 illustrates the X-ray powder diffractogram (XRD) of varenicline hemi-1,2-ethane disulfonate Form I obtained in Example 18.

FIG. 37 illustrates the Infrared (IR) spectra of varenicline hemi-L-lactate Form I obtained in Example 19.

FIG. 38 illustrates the X-ray powder diffractogram (XRD) of varenicline hemi-L-lactate Form I obtained in Example 19.

FIG. 39 illustrates the Infrared (IR) spectra of varenicline D-gluconate amorphous form obtained in Example 20.

FIG. 40 illustrates the X-ray powder diffractogram (XRD) of varenicline D-gluconate amorphous form obtained in Example 20.

FIG. 41 illustrates the Infrared (IR) spectra of varenicline malate Form II obtained in Example 46.

FIG. 42 illustrates the X-ray powder diffractogram (XRD) of varenicline malate Form II obtained in Example 46.

FIG. 43 illustrates the Infrared (IR) spectra of varenicline malate Form III obtained in Example 47.

FIG. 44 illustrates the X-ray powder diffractogram (XRD) of varenicline malate Form III obtained in Example 47.

FIG. 45 illustrates the Infrared (IR) spectra of varenicline malate Form IV obtained in Example 49.

FIG. 46 illustrates the X-ray powder diffractogram (XRD) of varenicline malate Form IV obtained in Example 49.

FIG. 47 illustrates the Infrared (IR) spectra of varenicline phosphate Form II obtained in Example 50.

FIG. 48 illustrates the X-ray powder diffractogram (XRD) of varenicline phosphate Form II obtained in Example 50.

FIG. 49 illustrates the Infrared (IR) spectra of varenicline phosphate Form III obtained in Example 55.

FIG. 50 illustrates the X-ray powder diffractogram (XRD) of varenicline phosphate Form III obtained in Example 55.

FIG. 51 illustrates the Infrared (IR) spectra of varenicline hydrochloride Form II obtained in Example 56.

FIG. 52 illustrates the X-ray powder diffractogram (XRD) of varenicline hydrochloride Form II obtained in Example 56.

FIG. 53 illustrates the Infrared (IR) spectra of varenicline hydrochloride Form III obtained in Example 66.

FIG. 54 illustrates the X-ray powder diffractogram (XRD) of varenicline hydrochloride Form III obtained in Example 66.

FIG. 55 illustrates the simulated X-ray diffractogram (XR) for single crystal of varenicline fumarate Form I.

FIG. 56 illustrates the molecular structure of varenicline fumarate Form I with the atom-labelling scheme.

SUMMARY OF THE INVENTION

The present invention relates generally to novel salt forms of 7,8,9,10-tetrahydro-6,10-methano-6H-pyrazino[2,3-h][3] benzazepine, i.e. varenicline base, to processes for their preparation and isolation, and to pharmaceutical compositions comprising the same.

DETAILED DESCRIPTION OF THE INVENTION

It has been found that varenicline can exist in a number of crystalline salt forms.

The novel crystalline salt forms of varenicline of the present invention have been prepared and characterized as described herein and are referred to herein as varenicline hemi-adipate (Form I), fumarate (Form I), glutarate (Form I), glycolate (Form I), hydrochloride (Forms I, and III), α-ketoglutarate (Form I), L-malate (Forms I, II, III, and IV), maleate (Form I), malonate (Form I), DL-mandelate (Form I), di-(methane sulfonate) (Form I), oxalate (Form I), phosphate (Forms I, II, and III), S-2-pyrrolidinon-5-carboxylate (Form I), galactarate (Form I), DL-lactate (Form I), hemi-1,2-ethane disulfonate (Form I), and hemi-L-lactate (Form I).

Also, it has been found that varenicline can exist in one amorphous salt form.

The novel amorphous salt form of varenicline of the present invention has been prepared and characterized as described herein and is referred to herein as varenicline D-gluconate amorphous Form.

The novel salt forms of varenicline of the present invention exhibit a high solubility profile in water, i.e. higher than approximately 20 mg/mL, which might enhance their pharmaceutical properties such as dissolution rate and bioavailability. Further, the formation of the varenicline salts of the invention might be an efficient way of purifying varenicline base. In addition, a number of the crystalline salt forms of varenicline of the present invention have been found to be highly stable in terms of chemical purity and of polymorphic form after one year of storage, which makes them more suitable for pharmaceutical formulation use.

The solid form salts of varenicline of the present invention have been characterized by means of Fourier Transform Infrared (FTIR) spectra, Powder X-ray diffraction pattern (XRD), Proton Nuclear Magnetic Resonance ($^1$H NMR) and High Performance Liquid Chromatography (HPLC).

A first aspect of the present invention includes varenicline hemi-adipate crystalline salt form (Form I), and processes for its preparation and isolation.

The varenicline hemi-adipate Form I of the present invention shows an IR spectrum having its main peaks at 2947.3, 2933.6, 2916.6, 1596.4, 1472.5, 1444.1, 1385.8, 1365.2, 1270.5, 1253.1, 1029.3, 940.1, 917.6, 884.8, 761.5, 518.3 and 500.7 cm$^{-1}$ with further peaks at 3399.3, 2761.3, 2546.5, 2371.3, 1951.8, 1720.0, 1412.7, 1305.7, 1196.1, 1185.5, 1160.8, 1149.7, 1128.8, 1091.1, 1060.7, 1013.5, 898.5, 864.6, 797.2, 782.5, 727.0, 634.8, 601.2 and 592.2 cm$^{-1}$. FIG. 1 illustrates the IR spectrum of varenicline hemi-adipate Form I.

The varenicline hemi-adipate Form I of the present invention shows an XRD pattern (2θ) (±0.2°) having characteristics peaks at 10.8, 14.6, 17.1, 17.7, 18.4, 18.7, 22.0, 23.4 and 25.8° with further peaks at 9.9, 11.8, 14.9, 21.6, 22.8, 25.1, 26.8, 27.8, 28.4, 28.8, 29.0, 30.5, 30.8, 31.5, 32.6 and 36.0°. FIG. 2 illustrates the XRD of varenicline hemi-adipate Form I.

The hemi-salt (2:1) correlation of varenicline hemi-adipate Form I was confirmed by $^1$H NMR spectrum.

The varenicline hemi-adipate Form I of the invention has a purity higher than about 99.8% relative peak area by HPLC. In addition, the varenicline hemi-adipate Form I of the invention is highly soluble in water. Also, the varenicline hemi-adipate Form I of the invention has been found to be highly stable in terms of chemical purity and of polymorphic form after one year of storage.

Another aspect of the invention relates to a process for preparing varenicline hemi-adipate salt Form I, said process comprising contacting varenicline with adipic acid, optionally in the presence of a suitable solvent, and removing the solvent when necessary.

The suitable solvent preferably comprises a $C_1$-$C_5$ alcohol solvent or mixtures thereof. More preferably, the suitable solvent is 2-propanol.

Another aspect of the present invention includes varenicline hemi-1,2-ethanedisulfonate crystalline salt form (Form I), and processes for its preparation and isolation.

The varenicline hemi-1,2-ethane disulfonate Form I of the present invention shows an IR spectrum having its main peaks at 3355.6, 3007.9, 2977.7, 2847.8, 2799.8, 2775.2, 2727.6, 2572.5, 2343.4, 2103.7, 2036.6, 1527.1, 1461.4, 1233.9, 1205.0, 1148.7, 1033.5, 914.6, 873.9, 597.8, 547.6, 526.3 and 498.2 cm$^{-1}$ with further peaks at 3246.8, 3061.8, 2682.7, 1918.4, 1642.7, 1618.5, 1584.9, 1570.9, 1472.9, 1377.0, 1362.4, 1348.3, 1315.4, 1291.6, 1271.1, 903.7, 840.2, 794.2, 774.5 and 723.0 cm$^{-1}$. FIG. 35 illustrates the IR spectrum of varenicline hemi-1,2-ethane disulfonate Form I.

The varenicline hemi-1,2-ethane disulfonate Form I of the present invention shows an XRD pattern (2θ) (±0.2°) having characteristics peaks at 15.6, 16.3, 18.3, 18.8, 19.4, 20.1, 20.6, 21.6, 22.5, 25.6, 28.0 and 32.9° with further peaks at 13.6, 15.0, 17.3, 17.5, 23.9, 24.7, 27.3, 28.9, 30.2 and 34.6°. FIG. 36 illustrates the XRD of varenicline hemi-1,2-ethane disulfonate Form I.

The hemi-salt (2:1) correlation of varenicline hemi-1,2-ethane disulfonate Form I was confirmed by $^1$H NMR spectrum.

The varenicline hemi-1,2-ethane disulfonate Form I of the invention has a purity higher than about 99.6% relative peak area by HPLC.

Another aspect of the invention relates to a process for preparing varenicline hemi-1,2-ethane disulfonate salt Form I, said process comprising contacting varenicline with 1,2-ethane disulfonic acid, optionally in the presence of a suitable solvent, and removing the solvent when necessary. The 1,2-ethane disulfonic acid can be optionally prepared in-situ from disodium 1,2-ethane disulfonate.

The suitable solvent preferably comprises a $C_1$-$C_5$ alcohol solvent or mixtures thereof. More preferably, the suitable solvent is 2-propanol.

Another aspect of the present invention includes varenicline fumarate crystalline salt form (Form I), and processes for its preparation and isolation.

The varenicline fumarate Form I of the present invention shows an IR spectrum having its main peaks at 2972.9, 2798.6, 1703.6, 1612.3, 1475.1, 1392.2, 1357.8, 1259.9, 1172.1, 1089.6, 1026.5, 984.6, 936.3, 916.7, 891.2, 793.0, 637.0, 559.2 and 503.2 cm$^{-1}$ with further peaks at 3393.9, 2621.8, 1634.3, 777.0, 748.0, 718.4, 667.4, 600.7 and 590.7 cm$^{-1}$. FIG. 3 illustrates the IR spectrum of varenicline fumarate Form I.

The varenicline fumarate Form I of the present invention shows an XRD pattern (2θ) (±0.2°) having characteristics peaks at 10.6, 11.9, 13.2, 16.2, 16.6, 18.0, 21.5, 22.6, 25.7, 28.5 and 29.1° with further peaks at 7.1, 11.2, 13.8, 14.4, 19.3, 20.5, 22.3, 24.1, 24.5, 24.9, 27.8 and 31.8°. FIG. 4 illustrates the XRD of varenicline fumarate Form I.

The 1:1 salt correlation of varenicline fumarate Form I was confirmed by $^1$H NMR spectrum.

The varenicline fumarate Form I of the invention has a purity higher than about 99.8% relative peak area by HPLC. In addition, the varenicline fumarate Form I of the invention is highly soluble in water. Also, the varenicline fumarate Form I of the invention has been found to be highly stable in terms of chemical purity and of polymorphic form after one year of storage.

FIG. 56 illustrates the molecular structure of varenicline fumarate Form I with the atom-labelling scheme. The basic crystallographic data for single crystal of varenicline fumarate Form I is as follows:

| | |
|---|---|
| Crystal Size | 0.60 × 0.45 × 0.45 mm$^3$ |
| Crystal system, space group | Triclinic, P-1 |
| Unit Cell dimensions | a = 8.3288(9) Å |
| | b = 12.322(2) Å |
| | c = 15.533(4) Å |
| | α = 88.06(2)° |
| | β = 88.989(10)° |
| | γ = 80.987(10)° |
| Volume | 1573.4(5) Å$^3$ |
| Z | 4 |
| Calculated density | 1.382 Mg/m$^3$ |

FIG. 55 illustrates a simulated X-ray diffractogram which has been calculated using the crystallographic data for single crystal of varenicline fumarate Form I. The simulated X-ray diffractogram of FIG. 55 is substantially similar to the X-ray powder diffractogram of varenicline fumarate Form I of FIG. 4.

Another aspect of the invention relates to a process for preparing varenicline fumarate salt Form I, said process comprising contacting varenicline with fumaric acid, optionally in the presence of a suitable solvent, and removing the solvent when necessary.

Another further aspect of the invention relates to a process for preparing varenicline fumarate salt Form I, said process comprising contacting varenicline fumarate salt with a suitable solvent, and removing the solvent.

The suitable solvent of the processes above preferably comprises a $C_1$-$C_5$ alcohol solvent, a ketone solvent, an haloalkane solvent, an ether solvent, an ester solvent, mixtures thereof, or mixtures thereof with water. More preferably, the suitable solvent comprises at least one of the group consisting of acetone, 2-butanone, methyl isobutyl ketone, chloroform, methanol, ethanol, isopropyl alcohol, methyl tert-butyl ether, tetrahydrofuran, isopropyl acetate, and ethanol/water 80:20.

Another aspect of the present invention includes varenicline glutarate crystalline salt form (Form I), and processes for its preparation and isolation.

The varenicline glutarate Form I of the present invention shows an IR spectrum having its main peaks at 2957.5, 2802.5, 2591.9, 1721.7, 1578.8, 1475.4, 1405.9, 1257.2, 1169.8 and 504.6 cm$^{-1}$ with further peaks at 3412.0, 1978.2, 1614.0, 1462.8, 1358.7, 1319.0, 1132.5, 1089.5, 1068.0, 1034.2, 941.5, 917.6, 896.4, 871.7, 809.8, 779.0, 758.6, 720.3 and 589.0 cm$^{-1}$. FIG. 5 illustrates the IR spectrum of varenicline glutarate Form I.

The varenicline glutarate Form I of the present invention shows an XRD pattern (2θ) (±0.2°) having characteristics peaks at 8.9, 10.3, 11.5, 14.1, 14.5, 15.4, 17.2, 17.7, 18.3, 19.7, 21.6, 22.1, 22.6, 24.3, 24.9, 25.7, 27.4 and 28.1° with further peaks at 7.6, 13.3, 29.7, 30.9, 31.5 and 32.3°. FIG. 6 illustrates the XRD of varenicline glutarate Form I.

The 1:1 salt correlation of varenicline glutarate Form I was confirmed by $^1$H NMR spectrum.

The varenicline glutarate Form I of the invention has a purity higher than about 98.7% relative peak area by HPLC.

Another aspect of the invention relates to a process for preparing varenicline glutarate salt Form I, said process comprising contacting varenicline with glutaric acid, optionally in the presence of a suitable solvent, and removing the solvent when necessary.

The suitable solvent preferably comprises a $C_1$-$C_5$ alcohol solvent or mixtures thereof. More preferably, the suitable solvent is 2-propanol.

Another aspect of the present invention includes varenicline glycolate crystalline salt form (Form I), and processes for its preparation and isolation.

The varenicline glycolate Form I of the present invention shows an IR spectrum having its main peaks at 3262.6, 2966.6, 2800.1, 2588.3, 1690.5, 1580.5, 1474.8, 1445.0, 1356.9, 1262.4, 1209.7 and 1089.4 cm$^{-1}$ with further peaks at 1878.6, 1406.7, 1377.6, 1319.3, 1306.0, 1287.4, 1234.0, 1194.5, 1149.5, 1031.9, 989.4, 945.1, 914.7, 902.5, 888.5, 873.4, 782.2, 676.3 and 506.9 cm$^{-1}$. FIG. 7 illustrates the IR spectrum of varenicline glycolate Form I.

The varenicline glycolate Form I of the present invention shows an XRD pattern (2θ) (±0.2°) having characteristics peaks at 6.8, 12.4, 17.8, 19.5, 23.5, 26.5, 27.6 and 29.5° with further peaks at 10.1, 10.4, 13.8, 14.5, 15.8, 18.8, 20.6, 22.1, 22.8, 25.2, 29.9, 30.6, 31.8, 33.7, 34.9, 36.1, 37.0 and 39.9°. FIG. 8 illustrates the XRD of varenicline glycolate Form I.

The 1:1 salt correlation of varenicline glycolate Form I was confirmed by $^1$H NMR spectrum.

The varenicline glycolate Form I of the invention has a purity higher than about 99.9% relative peak area by HPLC.

Another aspect of the invention relates to a process for preparing varenicline glycolate salt Form I, said process comprising contacting varenicline with glycolic acid, optionally in the presence of a suitable solvent, and removing the solvent when necessary.

The suitable solvent preferably comprises a $C_1$-$C_5$ alcohol solvent or mixtures thereof. More preferably, the suitable solvent is 2-propanol.

Another aspect of the present invention includes varenicline hydrochloride salt in new crystalline forms (Forms I, and III), and processes for their preparation and isolation.

The crystalline forms of varenicline hydrochloride obtained by the processes of the invention have been characterized herein and are referred to herein as varenicline hydrochloride Forms I, and III.

The varenicline hydrochloride Form I of the present invention shows an IR spectrum having its main peaks at 3407.4, 3353.0, 3060.5, 3007.7, 2978.1, 2914.3, 2846.3, 2799.6, 2772.6, 2727.2, 2683.5, 2628.5, 2571.5, 2328.2, 2102.7, 2035.2, 1569.8, 1526.6, 1472.7, 1460.9, 1347.6, 1204.8, 1148.5, 1043.2, 915.3, 874.4 and 597.6 cm$^{-1}$ with further peaks at 3247.5, 1916.5, 1643.8, 1617.0, 1585.1, 1377.2, 1362.8, 1314.6, 1291.1, 1277.0, 1059.3, 1032.6, 1007.0, 840.4 and 522.8 cm$^{-1}$. FIG. 9 illustrates the IR spectrum of varenicline hydrochloride Form I.

The varenicline hydrochloride Form I of the present invention shows an XRD pattern (2θ) (±0.2°) having characteristics peaks at 9.4, 16.4, 17.3, 20.7, 21.7, 24.0, 25.6, 27.4, 28.1, 29.0, 32.9 and 34.7° with further peaks at 15.2, 15.8, 16.9, 18.4, 18.8, 19.1, 19.7, 21.9, 24.8, 32.6, 36.8, 37.3 and 39.6°. FIG. 10 illustrates the XRD of varenicline hydrochloride Form I.

The varenicline hydrochloride Form I of the invention has a purity higher than about 99.8% relative peak area by HPLC.

Another aspect of the invention relates to a process for preparing varenicline hydrochloride salt Form I, said process comprising contacting varenicline with hydrochloric acid, in the presence of isopropanol, and removing the isopropanol from the mixture.

The present inventors have reproduced the preparation of the hydrochloride salt of varenicline described in Example 26 of U.S. Pat. No. 6,410,550. In particular, the varenicline hydrochloride obtained after crystallization from methanol/diethyl ether has been isolated and characterized herein, and has been denominated herein as Form II (See Comparative Example 1).

The varenicline hydrochloride known Form II shows an IR spectrum having its main peaks at 3395.6, 3027.4, 2797.3, 2615.1, 1606.9, 1479.6, 1456.6, 1356.7, 1155.4, 1032.5, 942.9, 917.5, 892.2, 589.4, 507.4, 451.5, 419.9 cm$^{-1}$ with further peaks at 1410.2, 1320.8, 1290.6, 1265.8, 1207.0, 1190.9, 1134.4, 1090.4, 874.8, 780.3 cm$^{-1}$. FIG. 51 illustrates the IR spectrum of varenicline hydrochloride Form II.

The varenicline hydrochloride known Form II shows an XRD pattern (2θ) (±0.2°) having characteristics peaks at 6.1, 12.1, 14.4, 14.8, 15.2, 18.2, 19.3, 20.6, 22.4, 23.1, 24.3, 26.0, 27.4, 28.1, 29.8, 30.4, 32.0° with further peaks at 16.0, 17.7, 18.8, 23.4, 23.9, 25.2, 28.7°. FIG. 52 illustrates the XRD of varenicline hydrochloride Form II.

The preparation of varenicline hydrochloride salt Form II can be carried out by means of crystallization from methanol/diethyl ether or by contacting varenicline with hydrochloric acid in the presence of methyl tert-butyl ether, and removing the methyl tert-butyl ether from the mixture.

The varenicline hydrochloride Form III of the present invention shows an IR spectrum having its main peaks at 3395.9, 3027.7, 2798.4, 2614.1, 1605.9, 1479.8, 1457.0, 1356.9, 1320.9, 1155.8, 1033.7, 943.1, 917.9, 894.4, 589.1, 507.8 cm$^{-1}$ with further peaks at 1291.0, 1267.3, 1207.0, 1191.3, 1134.7, 1091.1, 875.2, 850.0, 780.8 cm$^{-1}$. FIG. 53 illustrates the IR spectrum of varenicline hydrochloride Form III.

The varenicline hydrochloride Form III of the present invention shows an XRD pattern (2θ) (±0.2°) having characteristics peaks at 8.2, 10.2, 10.8, 16.3, 17.2, 19.2, 19.4, 19.8, 20.6, 21.7, 26.6, 27.5, 29.8° with further peaks at 10.4, 11.0, 12.3, 13.2, 13.6, 16.7, 21.3, 22.7, 23.4, 24.8, 25.3, 28.2, 28.6, 29.0, 30.8°. FIG. 54 illustrates the XRD of varenicline hydrochloride Form III.

Another aspect of the invention relates to a process for preparing varenicline hydrochloride salt Form III, said process comprising contacting varenicline hydrochloride with a suitable solvent, and removing the solvent.

The suitable solvent preferably comprises at lease one of the group consisting of acetone, 2-butanone, methyl isobutyl ketone, chloroform, methanol, ethanol, methyl tert-butyl ether, tetrahydrofuran, isopropyl acetate, and ethanol/water 80:20.

Another aspect of the present invention includes varenicline α-ketoglutarate crystalline salt form (Form I), and processes for its preparation and isolation.

The varenicline α-ketoglutarate Form I of the present invention shows an IR spectrum having its main peaks at 2952.6, 2817.0, 2598.6, 1716.7, 1632.6, 1589.0, 1479.6, 1463.9, 1453.2, 1421.4, 1358.9, 1293.1, 1197.2, 1030.5, 943.8 and 919.3 cm$^{-1}$ with further peaks at 3416.5, 1872.9, 1154.1, 1097.7, 1086.4, 1062.8, 879.3, 844.0, 820.3, 783.5, 742.9, 727.4, 697.3, 638.1, 618.6, 590.4 and 503.5 cm$^{-1}$. FIG. 11 illustrates the IR spectrum of varenicline α-ketoglutarate Form I.

The varenicline α-ketoglutarate Form I of the present invention shows an XRD pattern (2θ) (±0.2°) having characteristics peaks at 8.8, 11.3, 11.5, 11.9, 12.4, 13.2, 13.9, 14.6, 17.0, 17.4, 17.8, 18.4, 19.9, 20.3, 20.9, 21.5, 22.5, 25.1, 25.7, 26.7, 27.0, 29.2 and 29.6° with further peaks at 12.4, 13.2, 17.8, 18.4, 19.9, 20.9, 21.5, 25.1, 26.7, 27.0 and 29.6°. FIG. 12 illustrates the XRD of varenicline α-ketoglutarate Form I.

The 1:1 salt correlation of varenicline α-ketoglutarate Form I was confirmed by $^1$H NMR spectrum.

The varenicline α-ketoglutarate Form I of the invention has a purity higher than about 99.7% relative peak area by HPLC.

Another aspect of the invention relates to a process for preparing varenicline α-ketoglutarate salt Form I, said process comprising contacting varenicline with α-ketoglutaric acid, optionally in the presence of a suitable solvent, and removing the solvent when necessary.

The suitable solvent preferably comprises a $C_1$-$C_5$ alcohol solvent or mixtures thereof. More preferably, the suitable solvent is 2-propanol.

Another aspect of the present invention includes varenicline L-malate salt in different crystalline forms (Forms I, II, III, and IV), and processes for their preparation and isolation.

The crystalline forms of varenicline L-malate obtained by the processes of the invention have been characterized herein and are referred to herein as varenicline L-malate Forms I, II, III, and IV.

The varenicline L-malate Form I of the present invention shows an IR spectrum having its main peaks at 2680.3, 2588.6, 2424.5, 1454.2, 1357.0, 1130.8, 1090.9, 1029.9, 941.7, 918.0, 892.5, 873.7, 795.3 and 776.7 cm$^{-1}$ with further peaks at 3036.0, 2964.0, 2786.6, 2732.6, 1727.0, 1596.2, 1477.1, 1175.1 and 508.3 cm$^{-1}$. FIG. 13 illustrates the IR spectrum of varenicline L-malate Form I.

The varenicline L-malate Form I of the present invention shows an XRD pattern (2θ) (±0.2°) having characteristics peaks at 7.9, 13.1, 15.9, 18.1, 19.8, 20.1, 21.2, 23.3, 26.4, 27.9 and 28.4° with further peaks at 18.1, 19.8, 20.1, 21.2, 26.4 and 27.9°. FIG. 14 illustrates the XRD of varenicline L-malate Form I.

The 1:1 salt correlation of varenicline L-malate Form I was confirmed by $^1$H NMR spectrum.

The varenicline L-malate Form I of the invention has a purity higher than about 99.9% relative peak area by HPLC. In addition, the varenicline L-malate Form I of the invention is highly soluble in water. Also, the varenicline L-malate Form I of the invention has been found to be stable in terms of chemical purity after one year of storage.

Another aspect of the invention relates to a process for preparing varenicline L-malate salt Form I, said process comprising contacting varenicline with malic acid, optionally in the presence of a suitable solvent, and removing the solvent when necessary.

The suitable solvent preferably comprises a $C_1$-$C_5$ alcohol solvent or mixtures thereof. More preferably, the suitable solvent is 2-propanol.

The varenicline L-malate Form II of the present invention shows an IR spectrum having its main peaks at 3277.0, 2892.1, 2824.7, 1701.2, 1636.3, 1572.8, 1480.1, 1417.6, 1320.2, 1278.9, 1185.5, 1101.9, 1030.4, 939.0, 917.0, and 887.3 cm$^{-1}$ with further peaks at 3053.5, 2966.9, 2589.5, 2454.4, 2398.8, 1932.9, 1358.5, 1338.0, 1158.5, 1136.1, 1010.1, 899.6, 782.5, 757.0, 668.4, 601.7, 590.6, and 506.4 cm$^{-1}$. FIG. 41 illustrates the IR spectrum of varenicline L-malate Form II.

The varenicline L-malate Form II of the present invention shows an XRD pattern (2θ) (±0.2°) having characteristics peaks at 6.1, 11.6, 12.7, 16.7, 16.8, 19.0, 22.2, and 24.7° with further peaks at 12.2, 14.5, 18.5, 19.7, 20.6, 21.4, 21.7, 25.3, 27.2, and 32.6°. FIG. 42 illustrates the XRD of varenicline L-malate Form II.

The varenicline L-malate Form II of the invention has a purity higher than about 99.9% relative peak area by HPLC. The varenicline L-malate Form II of the invention has been found to be highly stable in terms of chemical purity and of polymorphic form after one year of storage.

Another aspect of the invention relates to a process for preparing varenicline L-malate salt Form II, said process comprising contacting varenicline L-malate with a suitable solvent, and removing the solvent.

The suitable solvent preferably comprises at lease one of the group consisting of 2-butanone, methyl isobutyl ketone, chloroform, methyl tert-butyl ether, tetrahydrofuran, isopropyl acetate, and mixtures thereof.

The varenicline L-malate Form III of the present invention shows an IR spectrum having its main peaks at 3419, 2970, 2814, 2616, 1717, 1636, 1602, 1479, 1436, 1401, 1356, 1297, 1269, 1205, 1182, 1134, 1105, 1027, 937, 910, 890, 776, 698, 641, 601, 544, 500, and 445 cm$^{-1}$. FIG. 43 illustrates the IR spectrum of varenicline L-malate Form III.

The varenicline L-malate Form III of the present invention shows an XRD pattern (2θ) (±0.2°) having characteristics peaks at 6.2, 11.5, 12.3, 12.6, 13.7, 14.4, 16.5, 17.1, 18.7, 19.1, 19.8, 21.1, 22.0, 23.1, 23.4, 24.6, 25.1, 26.3, 27.6, 29.5, 31.4, and 38.8°. FIG. 44 illustrates the XRD of varenicline L-malate Form III.

Another aspect of the invention relates to a process for preparing varenicline L-malate Form III, said process comprising contacting varenicline with L-malic acid, in the presence of a $C_1$-$C_5$ alcohol solvent, and removing the solvent.

Another aspect of the invention relates to a process for preparing varenicline L-malate salt Form III, said process comprising contacting varenicline L-malate with a $C_1$-$C_5$ alcohol solvent, and removing the solvent.

The $C_1$-$C_5$ alcohol solvent of the processes above preferably comprises 2-propanol, methanol, or mixtures thereof.

The varenicline L-malate Form IV of the present invention shows an IR spectrum having its main peaks at 3439, 2974, 2876, 2827, 2620, 2462, 1629, 1475, 1409, 1357, 1323, 1292, 1209, 1189, 1157, 1103, 1029, 937, 891, 776, 664, 604, 546, 504, 483, and 454 cm$^{-1}$. FIG. 45 illustrates the IR spectrum of varenicline L-malate Form IV.

The varenicline L-malate Form IV of the present invention shows an XRD pattern (2θ) (±0.2°) having characteristics peaks at 6.0, 11.2, 13.6, 15.3, 16.1, 17.2, 18.4, 21.0, 22.7, 24.2, 24.7, 26.5, 27.6, and 29.1°. FIG. 46 illustrates the XRD of varenicline L-malate Form IV.

Another aspect of the invention relates to a process for preparing varenicline L-malate Form IV, said process comprising contacting varenicline L-malate with a mixture of ethanol/water 90:10, and removing the solvent.

Another aspect of the present invention includes varenicline maleate crystalline salt form (Form I), and processes for its preparation and isolation.

The varenicline maleate Form I of the present invention shows an IR spectrum having its main peaks at 3054.1, 2961.3, 2820.5, 2601.1, 1588.3, 1478.8, 1454.8, 1373.5, 1348.0, 1323.1, 1088.0, 1027.8, 977.9, 936.1, 918.6, 886.3, 855.3, 692.0 and 553.0 cm$^{-1}$ with further peaks at 3411.9, 2446.7, 1250.7, 1208.6, 1192.9, 1172.9, 1141.2, 794.6 and 777.0 cm$^{-1}$. FIG. 15 illustrates the IR spectrum of varenicline maleate Form I.

The varenicline maleate Form I of the present invention shows an XRD pattern (2θ) (±0.2°) having characteristics peaks at 13.5, 16.7, 18.1, 18.2, 25.6, 28.5 and 29.0° with further peaks at 11.3, 14.1, 15.1, 22.3, 23.1, 28.0 and 30.1°. FIG. 16 illustrates the XRD of varenicline maleate Form I.

The 1:1 salt correlation of varenicline maleate Form I was confirmed by $^1$H NMR spectrum.

The varenicline maleate Form I of the invention has a purity higher than about 99.9% relative peak area by HPLC. In addition, the varenicline maleate Form I of the invention is highly soluble in water. Also, the varenicline maleate Form I of the invention has been found to be highly stable in terms of chemical purity and of polymorphic form after one year of storage.

Another aspect of the invention relates to a process for preparing varenicline maleate salt Form I, said process comprising contacting varenicline with maleic acid, optionally in the presence of a suitable solvent, and removing the solvent when necessary.

The suitable solvent preferably comprises a $C_1$-$C_5$ alcohol solvent, a ketone solvent, an haloalkane solvent, an ether solvent, an ester solvent, mixtures thereof, or mixtures thereof with water. More preferably, the suitable solvent comprises at lease one of the group consisting of acetone, 2-butanone, methyl isobutyl ketone, chloroform, methanol, ethanol, isopropyl alcohol, methyl tert-butyl ether, tetrahydrofuran, isopropyl acetate, and ethanol/water 80:20.

Another aspect of the present invention includes varenicline malonate crystalline salt form (Form I), and processes for its preparation and isolation.

The varenicline malonate Form I of the present invention shows an IR spectrum having its main peaks at 2794.6, 2744.4, 2589.4, 1730.8, 1618.2, 1471.7, 1453.8, 1440.4, 1359.2, 1343.6, 1172.8 and 505.4 cm$^{-1}$ with further peaks at 3398.0, 3328.7, 3119.4, 2960.3, 2918.0, 2695.6, 1928.1, 1396.3, 1269.4, 1200.9, 1090.5, 1060.0, 1030.2, 946.3, 938.1, 917.0, 900.6, 875.2, 778.4, 748.5, 656.6, 621.4 and 586.5 cm$^{-1}$. FIG. 17 illustrates the IR spectrum of varenicline malonate Form I.

The varenicline malonate Form I of the present invention shows an XRD pattern (2θ) (±0.2°) having characteristics peaks at 16.4, 22.2, 25.5 and 27.5° with further peaks at 11.1, 11.3, 13.0, 13.4, 14.4, 15.0, 16.6, 17.4, 17.9, 18.5, 19.1, 20.4, 20.8, 22.6, 23.5, 24.2, 24.9, 26.1, 28.1, 29.5, 30.2 and 31.1°. FIG. 18 illustrates the XRD of varenicline malonate Form I.

The 1:1 salt correlation of varenicline malonate Form I was confirmed by $^1$H NMR spectrum.

The varenicline malonate Form I of the invention has a purity higher than about 99.9% relative peak area by HPLC.

Another aspect of the invention relates to a process for preparing varenicline malonate salt Form I, said process comprising contacting varenicline with malonic acid, optionally in the presence of a suitable solvent, and removing the solvent when necessary.

The suitable solvent preferably comprises a $C_1$-$C_5$ alcohol solvent or mixtures thereof. More preferably, the suitable solvent is 2-propanol.

Another aspect of the present invention includes varenicline mandelate crystalline salt form (Form I), and processes for its preparation and isolation.

The varenicline DL-mandelate Form I of the present invention shows an IR spectrum having its main peaks at 3054.1, 2955.1, 2854.5, 2777.8, 2729.2, 2574.0, 2456.5, 2415.9, 1589.7, 1475.2, 1452.2, 1371.0, 1359.9, 1329.6, 1186.1, 1103.2, 1062.6, 939.5, 733.9, 700.9, 524.8, 507.7 and 501.7 cm$^{-1}$ with further peaks at 3339.6, 3232.0, 1736.9, 1713.9, 1298.5, 1267.3, 1252.3, 1236.9, 1218.2, 1208.4, 1165.4, 1155.2, 1131.6, 1091.1, 1040.6, 1028.7, 1022.3, 916.9, 895.7, 885.6, 774.3, 663.3, 604.3, 588.7 and 566.6 cm$^{-1}$. FIG. 19 illustrates the IR spectrum of varenicline DL-mandelate Form I.

The varenicline DL-mandelate Form I of the present invention shows an XRD pattern (2θ) (±0.2°) having characteristics peaks at 8.0, 12.0, 15.7, 17.2, 18.7, 19.5, 21.9 and 24.2° with further peaks at 4.6, 9.5, 11.4, 13.3, 13.9, 14.8, 16.3, 20.3, 23.4, 26.6, 27.2, 28.0, 28.8 and 30.7°. FIG. 20 illustrates the XRD of varenicline DL-mandelate Form I.

The 1:1 salt correlation of varenicline DL-mandelate Form I was confirmed by $^1$H NMR spectrum.

The varenicline DL-mandelate Form I of the invention has a purity higher than about 99.9% relative peak area by HPLC.

Another aspect of the invention relates to a process for preparing varenicline DL-mandelate salt Form I, said process comprising contacting varenicline with DL-mandelic acid, optionally in the presence of a suitable solvent, and removing the solvent when necessary.

The suitable solvent preferably comprises a $C_1$-$C_5$ alcohol solvent or mixtures thereof. More preferably, the suitable solvent is 2-propanol.

Another aspect of the present invention includes varenicline di-mesylate[di-(methanesulfonate)]crystalline salt form (Form I), and processes for its preparation and isolation.

The varenicline di-mesylate Form I of the present invention shows an IR spectrum having its main peaks at 3433.7, 3371.8, 3062.2, 3006.8, 2974.8, 2963.1, 2931.2, 2799.4, 2536.8, 1239.8, 1192.3, 1149.1, 1058.2, 784.5, 598.6, 562.1, 535.9 and 525.3 cm$^{-1}$ with further peaks at 3239.1, 2863.3, 2777.0, 2726.5, 2675.5, 2066.3, 2002.2, 1636.6, 1623.7, 1572.5, 1527.4, 1472.5, 1459.5, 1434.9, 1361.4, 1347.6, 1328.2, 1315.2, 1291.7, 1276.2, 1005.6, 913.8, 872.2 and 773.0 cm$^{-1}$. FIG. 21 illustrates the IR spectrum of varenicline di-mesylate Form I.

The varenicline di-mesylate Form I of the present invention shows an XRD pattern (2θ) (±0.2°) having characteristics peaks at 7.7, 15.5, 18.3, 18.5, 22.7, 23.3 and 26.2° with further peaks at 12.8, 13.5, 14.7, 18.9, 19.8, 23.9, 25.0, 25.7, 26.9, 28.8, 30.3, 33.7 and 42.2°. FIG. 22 illustrates the XRD of varenicline di-mesylate Form I.

The 1:2 salt correlation of varenicline di-mesylate Form I was confirmed by $^1$H NMR spectrum.

The varenicline di-mesylate Form I of the invention has a purity higher than about 99.9% relative peak area by HPLC.

Another aspect of the invention relates to a process for preparing varenicline di-mesylate salt Form I, said process comprising contacting varenicline with methane sulfonic acid, optionally in the presence of a suitable solvent, and removing the solvent when necessary.

The suitable solvent preferably comprises a $C_1$-$C_5$ alcohol solvent or mixtures thereof. More preferably, the suitable solvent is 2-propanol.

Another aspect of the present invention includes varenicline oxalate crystalline salt form (Form I), and processes for its preparation and isolation.

The varenicline oxalate Form I of the present invention shows an IR spectrum having its main peaks at 2945.6, 2758.3, 2560.0, 2396.2, 1713.4, 1598.9, 1505.7, 1471.9, 1449.3, 1400.7, 1358.7, 1217.1, 1206.8, 1191.9, 1156.2, 1036.9, 1029.0, 943.8, 912.6, 902.5, 732.9, 721.1 and 504.5 cm$^{-1}$ with further peaks at 3418.6, 2970.2, 2878.3, 1918.7, 1373.2, 1316.0, 1303.9, 1295.7, 1285.0, 1275.6, 1256.1, 1134.0, 1093.7, 1061.9, 1014.4, 863.6, 846.4, 799.8, 785.6, 621.9 and 593.3 cm$^{-1}$. FIG. 23 illustrates the IR spectrum of varenicline oxalate Form I.

The varenicline oxalate Form I of the present invention shows an XRD pattern (2θ) (±0.2°) having characteristics peaks at 10.7, 13.2, 13.4, 14.5, 15.4, 17.8, 19.4, 19.9, 21.4, 21.7, 22.4, 23.8, 26.5, 26.9, 30.4 and 32.6° with further peaks at 16.9, 18.6, 25.2, 28.6 and 34.9°. FIG. 24 illustrates the XRD of varenicline oxalate Form I.

The varenicline oxalate Form I of the invention has a purity higher than about 99.9% relative peak area by HPLC.

Another aspect of the invention relates to a process for preparing varenicline oxalate salt Form I, said process comprising contacting varenicline with oxalic acid, optionally in the presence of a suitable solvent, and removing the solvent when necessary.

The suitable solvent preferably comprises a $C_1$-$C_5$ alcohol solvent or mixtures thereof. More preferably, the suitable solvent is 2-propanol.

Another aspect of the present invention includes varenicline phosphate salt in different crystalline forms (Forms I, II, and III), and processes for their preparation and isolation.

The crystalline forms of varenicline phosphate obtained by the processes of the invention have been characterized herein and are referred to herein as varenicline phosphate Forms I, II, and III.

The varenicline phosphate Form I of the present invention shows an IR spectrum having its main peaks at 2834.2, 2381.8, 1613.4, 1474.1, 1208.7, 1107.1, 986.2, 942.8, 913.6 and 890.9 $cm^{-1}$ with further peaks at 1523.6, 1455.9, 1361.3, 1321.7 and 590.1 $cm^{-1}$. FIG. 25 illustrates the IR spectrum of varenicline phosphate Form I.

The varenicline phosphate Form I of the present invention shows an XRD pattern (2θ) (±0.2°) having characteristics peaks at 10.1, 15.7, 17.4, 19.2, 19.5, 20.1, 20.7, 21.4, 22.9 and 26.8° with further peaks at 6.3, 9.3, 11.0, 12.1, 13.3, 13.9, 14.6, 15.1, 16.5, 16.7, 20.3, 21.8, 24.0, 24.8, 25.4, 26.5, 27.7, 28.5, 29.1, 30.7 and 31.8°. FIG. 26 illustrates the XRD of varenicline phosphate Form I.

The varenicline phosphate Form I of the invention has a purity higher than about 99.9% relative peak area by HPLC. In addition, the varenicline phosphate Form I of the invention is highly soluble in water. Also, the varenicline phosphate Form I of the invention has been found to be highly stable in terms of chemical purity and in terms of polymorphic form after one year of storage.

Another aspect of the invention relates to a process for preparing varenicline phosphate salt Form I, said process comprising contacting varenicline with phosphoric acid, optionally in the presence of a suitable solvent, and removing the solvent when necessary.

The suitable solvent preferably comprises a $C_1$-$C_5$ alcohol solvent or mixtures thereof. More preferably, the suitable solvent is 2-propanol.

The varenicline phosphate Form II of the present invention shows an IR spectrum having its main peaks at 3392.7, 3040.3, 2835.1, 2367.3, 1635.6, 1558.9, 1476.4, 1457.0, 985.3, 942.9, 894.0, 507.0, 448.0, and 419.8 $cm^{-1}$. FIG. 47 illustrates the IR spectrum of varenicline phosphate Form II.

The varenicline phosphate Form II of the present invention shows an XRD pattern (2θ) (±0.2°) having characteristics peaks at 7.2, 7.5, 11.1, 15.7, 16.2, 16.8, 18.2, 18.7, 19.0, 19.3, 19.6, 19.8, 20.3, 21.7, 22.7, 23.0, 23.5, 23.9, 25.0, 25.3, 26.5, and 27.5° and with further peaks at 9.9, 11.8, 12.6, 13.1, 13.5, 14.6, 15.0, 17.4, 20.7, 21.1, 21.4, 22.0, 26.0, 27.1, 28.7, 29.9, 30.3, and 32.0°. FIG. 48 illustrates the XRD of varenicline phosphate Form II.

The varenicline phosphate Form II of the invention has a purity higher than about 99.8% relative peak area by HPLC. The varenicline phosphate Form II of the invention has been found to be highly stable in terms of chemical purity and in terms of polymorphic form after one year of storage.

Another aspect of the invention relates to a process for preparing varenicline phosphate salt Form II, said process comprising contacting varenicline phosphate with a suitable solvent, and removing the solvent.

The suitable solvent preferably comprises at lease one of the group consisting of 2-butanone, methyl isobutyl ketone, chloroform, methyl tert-butyl ether and isopropyl acetate.

The varenicline phosphate Form III of the present invention shows an IR spectrum having its main peaks at 3061, 2953, 2856, 2295, 1638, 1594, 1472, 1360, 1324, 1276, 1120, 1082, 1030, 981, 953, 941, 912, 896, 871, 844, 780, 726, 590, 527, 501, 482, and 444 $cm^{-1}$. FIG. 49 illustrates the IR spectrum of varenicline phosphate Form III.

The varenicline phosphate Form III of the present invention shows an XRD pattern (2θ) (±0.2°) having characteristics peaks at 7.1, 9.2, 10.4, 12.5, 13.6, 16.2, 17.4, 18.5, 18.8, 20.2, 21.2, 21.5, 22.0, 22.4, 23.1, 24.7, 27.6, 28.4, 29.5, and 43.4°. FIG. 50 illustrates the XRD of varenicline phosphate Form III.

Another aspect of the invention relates to a process for preparing varenicline phosphate salt Form III, said process comprising suspending varenicline phosphate in methanol, and removing the solvent.

Another aspect of the present invention includes varenicline S-2-pyrrolidinon-5-carboxylate (pyroglutamate) crystalline salt form (Form I), and processes for its preparation and isolation.

The varenicline pyroglutamate Form I of the present invention shows an IR spectrum having its main peaks at 3159.4, 3047.4, 2996.3, 2965.8, 2948.2, 2820.3, 1664.2, 1626.2, 1563.5, 1472.8, 1388.2, 1355.0, 1301.4, 1274.3, 918.7 and 502.3 $cm^{-1}$ with further peaks at 3426.2, 2561.9, 2384.6, 2199.1, 1439.8, 1206.4, 1186.1, 1161.1, 1142.8, 1133.6, 1089.7, 1042.6, 1027.3, 939.1, 886.3, 807.9, 778.5, 719.3 and 595.1 $cm^{-1}$. FIG. 27 illustrates the IR spectrum of varenicline pyroglutamate Form I.

The varenicline pyroglutamate Form I of the present invention shows an XRD pattern (2θ) (±0.2°) having characteristics peaks at 12.4, 15.9, 18.5, 19.0, 20.6, 23.2, 24.6, 25.5 and 29.5° with further peaks at 6.9, 14.0, 15.3, 23.8, 26.7, 27.7, 28.8, 33.9 and 35.3°. FIG. 28 illustrates the XRD of varenicline pyroglutamate Form I.

The 1:1 salt correlation of varenicline pyroglutamate Form I was confirmed by $^1$H NMR spectrum.

The varenicline pyroglutamate Form I of the invention has a purity higher than about 99.9% relative peak area by HPLC. In addition, the varenicline pyroglutamate Form I of the invention is highly soluble in water. Also, the varenicline pyroglutamate Form I of the invention has been found to be highly stable in terms of chemical purity and in terms of polymorphic form after one year of storage.

Another aspect of the invention relates to a process for preparing varenicline pyroglutamate salt Form I, said process comprising contacting varenicline with S-2-pyrrolidinon-5-carboxylic acid, optionally in the presence of a suitable solvent, and removing the solvent when necessary.

The suitable solvent preferably comprises a $C_1$-$C_5$ alcohol solvent or mixtures thereof. More preferably, the suitable solvent is 2-propanol.

Another aspect of the invention relates to a process for preparing varenicline succinate salt form, said process comprising i) contacting varenicline with succinic acid, in the presence of isopropanol, to obtain a mixture ii) heating the mixture at about 40° C. for 1 hour, iii) cooling the mixture at room temperature and stirring for 16 hours, and iv) removing the isopropanol from the mixture.

The varenicline succinate obtained by the process of the invention has a purity higher than about 99.9% relative peak area by HPLC.

Another aspect of the present invention includes varenicline galactarate crystalline salt form (Form I), and processes for its preparation and isolation.

The varenicline galactarate Form I of the present invention shows an IR spectrum having its main peaks at 3428.7, 3286.6, 3030.5, 2991.1, 2955.5, 2937.5, 2867.8, 2819.5, 2766.3, 2721.9, 2590.8, 1720.1, 1613.9, 1584.3, 1471.9, 1415.0, 1380.8, 1352.4, 1317.6, 1296.0, 1095.5, 1050.0, 1034.0, 1027.0, 937.1, 914.3, 895.0, 663.0, 519.6 and 505.7 cm$^{-1}$ with further peaks at 2454.1, 2393.0, 1457.2, 1441.7, 1239.1, 1206.9, 1185.8, 1151.7, 1008.7, 959.8, 882.3, 860.2, 824.6, 798.7, 779.6, 637.7, 603.6 and 592.2 cm$^{-1}$. FIG. 31 illustrates the IR spectrum of varenicline galactarate Form I.

The varenicline galactarate Form I of the present invention shows an XRD pattern (2θ) (±0.2°) having characteristics peaks at 7.2, 10.5, 12.1, 12.5, 13.0, 14.2, 16.8, 17.6, 18.2, 19.6, 21.2, 21.5, 21.8, 25.1, 29.3, 30.7 and 34.4° with further peaks at 22.9, 24.5, 26.0, 26.7, 27.2, 31.8 and 37.6°. FIG. 32 illustrates the XRD of varenicline galactarate Form I.

The 1:1 salt correlation of varenicline galactarate Form I was confirmed by $^1$H NMR spectrum.

The varenicline galactarate Form I of the invention has a purity higher than about 99.9% relative peak area by HPLC. In addition, the varenicline galactarate Form I of the invention is highly soluble in water. Also, the varenicline galactarate Form I of the invention has been found to be highly stable in terms of chemical purity and of polymorphic form after one year of storage.

Another aspect of the invention relates to a process for preparing varenicline galactarate salt Form I, said process comprising contacting varenicline with galactaric acid, optionally in the presence of a suitable solvent, and removing the solvent when necessary.

The suitable solvent preferably comprises a $C_1$-$C_5$ alcohol solvent or mixtures thereof. More preferably, the suitable solvent is 2-propanol.

Another aspect of the present invention includes varenicline DL-lactate crystalline salt form (Form I), and processes for its preparation and isolation.

The varenicline DL-lactate Form I of the present invention shows an IR spectrum having its main peaks at 3276.0, 3025.3, 2982.7, 2956.2, 2925.3, 2867.4, 1628.6, 1583.0, 1478.6, 1467.2, 1446.4, 1417.0, 1398.0, 1361.3, 1346.6, 1320.6, 1254.6, 1117.8, 1090.9, 1028.6, 941.0, 919.3, 636.5, 592.0 and 503.2 cm$^{-1}$ with further peaks at 2566.2, 2447.0, 2389.6, 2334.6, 1724.8, 1296.9, 1276.5, 1215.3, 1190.8, 1154.6, 1139.6, 1132.1, 1042.8, 884.1, 855.8, 842.4, 780.8, 770.6, 663.5, 607.4, 568.6 and 524.5 cm$^{-1}$. FIG. 33 illustrates the IR spectrum of varenicline DL-lactate Form I.

The varenicline DL-lactate Form I of the present invention shows an XRD pattern (2θ) (±0.2°) having characteristics peaks at 9.8, 14.8, 15.5, 17.3, 19.3, 19.8, 21.5, 21.8, 23.2, 25.1, 25.5 and 27.3° with further peaks at 15.9, 18.3, 26.9, 28.8, 29.7, 31.3 and 34.1°. FIG. 34 illustrates the XRD of varenicline DL-lactate Form I.

The 1:1 salt correlation of varenicline DL-lactate Form I was confirmed by $^1$H NMR spectrum.

The varenicline DL-lactate Form I of the invention has a purity higher than about 98.9% relative peak area by HPLC.

Another aspect of the invention relates to a process for preparing varenicline DL-lactate salt Form I, said process comprising contacting varenicline with DL-lactic acid, optionally in the presence of a suitable solvent, and removing the solvent when necessary.

The suitable solvent preferably comprises a $C_1$-$C_5$ alcohol solvent or mixtures thereof. More preferably, the suitable solvent is 2-propanol.

Another aspect of the present invention includes varenicline hemi-L-lactate crystalline salt form (Form I), and processes for its preparation and isolation.

The varenicline hemi-L-lactate Form I of the present invention shows an IR spectrum having its main peaks at 3246.7, 2977.0, 1616.8, 1568.8, 1478.5, 1423.5, 1370.1, 1239.7, 1129.8, 1090.6 and 1037.9 cm$^{-1}$ with further peaks at 1732.0, 942.1, 921.8, 899.4, 860.3, 823.4, 771.2, 620.7, 593.9 and 504.0 cm$^{-1}$. FIG. 37 illustrates the IR spectrum of varenicline hemi-L-lactate Form I.

The varenicline hemi-L-lactate Form I of the present invention shows an XRD pattern (2θ) (±0.2°) having characteristics peaks at 6.4, 9.8, 17.6, 18.3, 19.9, 22.6 and 25.2° with further peaks at 9.0, 11.2, 12.8, 13.6, 14.9, 15.6, 16.2, 19.1, 21.2, 23.1 and 29.0°. FIG. 38 illustrates the XRD of varenicline hemi-L-lactate Form I.

The hemi-salt (2:1) correlation of varenicline hemi-L-lactate Form I was confirmed by $^1$H NMR spectrum.

The varenicline hemi-L-lactate Form I of the invention has a purity higher than about 91.5% relative peak area by HPLC.

Another aspect of the invention relates to a process for preparing varenicline hemi-L-lactate salt Form I, said process comprising contacting varenicline with L-lactic acid, optionally in the presence of a suitable solvent, and removing the solvent when necessary.

The suitable solvent preferably comprises an ether solvent or mixtures thereof. More preferably, the suitable solvent is methyl tert-butyl ether.

Another aspect of the present invention includes varenicline D-gluconate salt in amorphous form, and processes for its preparation and isolation.

The varenicline D-gluconate amorphous form of the present invention shows an IR spectrum having its main peaks at 3383.6, 1600.0, 1477.8, 1408.9, 1358.2, 1087.1, 1032.2, 941.2 and 504.3 cm$^{-1}$ with further peaks at 1131.7, 916.4, 892.6 and 778.4 cm$^{-1}$. FIG. 39 illustrates the IR spectrum of varenicline D-gluconate Form I.

The varenicline D-gluconate of the present invention is substantially amorphous as characterized by XRD. FIG. 40 illustrates the XRD of varenicline D-gluconate amorphous form.

The 1:1 salt correlation of varenicline D-gluconate amorphous form was confirmed by $^1$H NMR spectrum.

The varenicline D-gluconate amorphous form of the invention has a purity higher than about 99.8% relative peak area by HPLC.

Another aspect of the invention relates to a process for preparing varenicline D-gluconate salt amorphous form, said process comprising contacting varenicline with D-gluconic acid, optionally in the presence of a suitable solvent, and removing the solvent when necessary.

The suitable solvent preferably comprises an ether solvent or mixtures thereof. More preferably, the suitable solvent is methyl tert-butyl ether.

The suitable solvents for carrying out the processes of the invention above can be at least one of the group consisting of dichloromethane, methyl tert-butyl ether (MTBE), n-butyl acetate, isopropyl acetate, toluene, heptane, dimethylformamide, tetrahydrofuran (THF), ethanol, 2-butanone, isopropanol, n-butanol, acetonitrile, methanol, methyl isobutyl ketone, and ethyl acetate.

Another aspect of the invention includes a formulation including the varenicline salts obtained according to the processes of the invention.

General Experimental Conditions:
X-ray Powder Diffraction (XRD)

The XRD diffractograms were obtained using a RX SIEMENS D5000 diffractometer with a vertical goniometer, a copper anodic tube, and radiation $CuK_\alpha$, $\lambda=1,54056$ Å.

Infrared Spectra (IR)

Fourier transform IR spectra were acquired on a Thermo Nicolet Nexus spectrometer, and samples were characterized in potassium bromide pellets.

Proton Nuclear Magnetic Resonance ($^1$H NMR)

Proton NMR spectra were determined at room temperature on Varian Mercury 400 MHz NMR spectrometer. All samples were prepared in $CDCl_3$ solution, with the exception of the varenicline gluconate salt which was prepared in d6-DMSO.

HPLC Method

The chromatographic separation was carried out with a ZORBAX Eclipse XDB-C18 5 μm 4.6×150 mm column with ZORBAX Eclipse XDB-C18 (4.6×12.5 mm) guard column at room temperature (20-25° C.). Mobile phase A was prepared by dissolving 1.3 g of ammonium formate in 1000 mL of water and adjusting the pH of the solution to 8.0±0.1 with ammonia 25%. The solution was then filtered through a 0.22 μm nylon membrane under vacuum. Mobile phase B was acetonitrile and filtered through a 0.22 μm nylon membrane under vacuum.

The flow rate was 1 mL per minute and the chromatograph was recorded at 230 nm. Test samples (10 μL) were prepared by dissolving the appropriate amount of sample in a 1:1 mixture of mobile phases A and B in order to obtain 1 mg of sample per mL. The following gradient was used:

| Time (min.) | % A | % B |
| --- | --- | --- |
| 0 | 95 | 5 |
| 5 | 95 | 5 |
| 35 | 60 | 40 |
| 45 | 60 | 40 |
| 50 | 95 | 5 |
| 55 | 95 | 5 |

Single Crystal X-Ray Analysis

X-ray data for single crystal of varenicline fumarate form I was collected at 293(2)K on an Enraf-Nonius CAD 4 diffractometer using Mo-$K_a$ radiation.

SPECIFIC EXAMPLES

Comparative Example 1

Preparation of Varenicline Hydrochloride Known Form II

This example has been carried out following the teachings of Example 26 of U.S. Pat. No. 6,410,550.

Varenicline hydrochloride (150 mg) was dissolved in methanol (0.7 mL) at reflux. Then, diethyl ether (2 mL) was added. The suspension was allowed to cool to ambient temperature and the solid was filtered.

XRD Analysis: Form II.

Examples 1-17

Preparation of Varenicline Salts

General procedure: varenicline base (100 mg) was stirred with isopropanol (1 mL) and one equivalent of acid was added before heating to 40° C. for 1 hour. The mixture was then allowed to cool to ambient temperature, stirred for 16 hours at this temperature before filtration and drying under vacuum at 40° C. Results are summarized in Table 1.

TABLE 1

| Example | Acid | quantity of acid (mg) | Purity (HPLC) | Solubility in water | Salt correlation (by $^1$H NMR) | XRD Analysis |
| --- | --- | --- | --- | --- | --- | --- |
| 1 | Adipic acid | 69 | 99.89% | >20 mg/mL | 1:2 salt | Form I |
| 2 | Fumaric acid | 55 | 99.84% | >20 mg/mL | 1:1 salt | Form I |
| 3 | glutaric acid | 63 | 98.77% | >20 mg/mL | 1:1 salt | Form I |
| 4 | Glycolic Acid | 36 | 99.95% | >20 mg/mL | 1:1 salt | Form I |
| 5 | Hydrochloric acid 37 wt % (12M) | 47 | 99.77% | >20 mg/mL | n.d.[a] | Form I |
| 6 | α-Ketoglutaric acid | 69 | 99.71% | >20 mg/mL | 1:1 salt | Form I |
| 7 | L-Malic acid | 64 | 99.95% | >20 mg/mL | 1:1 salt | Form I |
| 8 | Maleic acid | 55 | 100.00% | >20 mg/mL | 1:1 salt | Form I |
| 9 | Malonic acid | 49 | 99.91% | >20 mg/mL | 1:1 salt | Form I |
| 10 | DL-Mandelic acid | 72 | 99.93% | >20 mg/mL | 1:1 salt | Form I |
| 11 | Methane Sulfonic acid | 46 | 99.99% | >20 mg/mL | 2:1 salt | Form I |
| 12 | Oxalic acid anhydrous | 43 | 99.91% | >20 mg/mL | n.d.[a] | Form I |

TABLE 1-continued

| Example | Acid | quantity of acid (mg) | Purity (HPLC) | Solubility in water | Salt correlation (by ¹H NMR) | XRD Analysis |
|---|---|---|---|---|---|---|
| 13 | Phosphoric acid 85% wt | 55 | 100.00% | >20 mg/mL | n.d.[a] | Form I |
| 14 | S-2-Pyrrolidinon-5-carboxylic acid | 61 | 99.99% | >20 mg/mL | 1:1 salt | Form I |
| 15 | Succinic acid | 56 | 100.00% | >20 mg/mL | 1:1 salt | Form I |
| 16 | Galactaric acid | 100 | 99.91% | >20 mg/mL | 1:1 salt | Form I |
| 17 | DL-Lactic acid 85% aq solution | 50 | 98.98% | >20 mg/mL | 1:1 salt | Form I |

[a] Not determined value.

Example 18

Preparation of Varenicline Hemi-1,2-Ethane Disulfonate

Varenicline base (100 mg) was stirred with iso-propyl alcohol (1 mL) and one equivalent of disodium 1,2-ethane disulfonate (111 mg) and hydrochloric acid (37% aq, 93 mg) were added before heating to 40° C. for 1 hour. The mixture was then allowed to cool to ambient temperature, stirred for 16 hours at this temperature before filtration. The liquors were concentrated and dried under vacuum at 40° C. to give the product. HPLC purity: 99.61%; Solubility in water: >20 mg/mL; The hemi-salt (2:1) correlation of hemi-1,2-ethane disulfonate was confirmed by ¹H NMR spectrum.

Examples 19-20

Preparation of Varenicline Salts

General procedure: varenicline base (100 mg) was stirred with methyl tert-butyl ether (1 mL) and one equivalent of acid was added before heating to 40° C. for 1 hour. The mixture was then allowed to cool to ambient temperature, stirred for 16 hours at this temperature before filtration and drying under vacuum at 40° C. Results are summarized in Table 2.

TABLE 2

| Example | Acid | quantity of acid (mg) | Purity (HPLC) | Solubility in water | Salt correlation (by ¹H NMR) | XRD Analysis |
|---|---|---|---|---|---|---|
| 19 | L-Lactic acid 85% aq solution | 50 | 91.55% | >20 mg/mL | 2:1 salt | Form I |
| 20 | D-Gluconic Acid, 50% in water | 186 | 99.89% | >20 mg/mL | 1:1 salt | Amorphous form |

Examples 21-30

Preparation of Varenicline Fumarate Form I

General procedure: varenicline fumarate (140 mg) was suspended in the solvent (quantity as indicated in Table 3), and heated to reflux. In the case of methanol and water/ethanol complete dissolution was observed. The mixture was allowed to cool to ambient temperature, and stirred for 24 hours at this temperature before evaporation of the solvent. Results are summarized in Table 3.

TABLE 3

| Example | Solvent | Quantity (mL) | XRD Analysis |
|---|---|---|---|
| 21 | acetone | 3 mL | Form I |
| 22 | chloroform | 3 mL | Form I |
| 23 | methanol | 2 mL | Form I |
| 24 | MTBE | 3 mL | Form I |
| 25 | THF | 3 mL | Form I |
| 26 | ethanol | 3 mL | Form I |
| 27 | 2-butanone | 3 mL | Form I |
| 28 | Methyl i-butylketone | 3 mL | Form I |
| 29 | water/ethanol (20-80) | 0.8 mL | Form I |
| 30 | i-propyl acetate | 3 mL | Form I |

Examples 31-40

Preparation of Varenicline Maleate Form I

General procedure: varenicline maleate (140 mg) was suspended in the solvent (quantity as indicated in Table 4), and heated to reflux. In the case of ethanol, methanol and water/ethanol complete dissolution was observed. The mixture was allowed to cool to ambient temperature, and stirred for 24 hours at this temperature before evaporation of the solvent. Results are summarized in Table 4.

TABLE 4

| Example | Solvent | Quantity (mL) | XRD Analysis |
|---|---|---|---|
| 31 | acetone | 3 mL | Form I |
| 32 | chloroform | 3 mL | Form I |
| 33 | methanol | 0.5 mL | Form I |
| 34 | MTBE | 3 mL | Form I |
| 35 | THF | 3 mL | Form I |
| 36 | ethanol | 1.5 mL | Form I |
| 37 | 2-butanone | 3 mL | Form I |

TABLE 4-continued

| Example | Solvent | Quantity (mL) | XRD Analysis |
| --- | --- | --- | --- |
| 38 | Methyl i-butylketone | 3 mL | Form I |
| 39 | water/ethanol (20-80) | 0.2 mL | Form I |
| 40 | i-propyl acetate | 3 mL | Form I |

Examples 41-46

Preparation of Varenicline Malate Form II

General procedure: varenicline malate (140 mg) was suspended in the solvent (quantity as indicated in Table 5), and heated to reflux. The mixture was allowed to cool to ambient temperature, and stirred for 24 hours at this temperature before evaporation of the solvent. Results are summarized in Table 5.

TABLE 5

| Example | Solvent | Quantity | XRD Analysis |
| --- | --- | --- | --- |
| 41 | chloroform | 3 mL | Form II |
| 42 | MTBE | 3 mL | Form II |
| 43 | THF | 3 mL | Form II |
| 44 | 2-butanone | 3 mL | Form II |
| 45 | Methyl i-butylketone | 3 mL | Form II |
| 46 | i-propyl acetate | 3 mL | Form II |

Example 47

Preparation of Varenicline Malate Form III

To a solution of Varenicline base (1 g) in 2-propanol (15 mL) at 40° C., malic acid (1.55 g) was added. The resulting suspension was heated at 40° C. for 1 h and allowed to cool to ambient temperature for 5 h. Finally, the solid was filtered and dried at 40° C. under vacuum. HPLC purity: 99.70%; XRD Analysis: Form III.

Example 48

Preparation of Varenicline Malate Form III

Varenicline malate (150 mg) was dissolved in methanol (2.5 mL) at reflux. The solution was allowed to cool to ambient temperature overnight. The solid was filtered and analysed by XRD. HPLC purity: 99.73%; XRD Analysis: Form III.

Example 49

Preparation of Varenicline Malate Form IV

Varenicline malate (150 mg) was dissolved in a mixture of ethanol/water 90:10 (0.5 mL) at reflux for 1 h. The solution was allowed to cool to ambient temperature overnight. The solid was filtered and analysed by XRD. HPLC purity: 99.5; XRD Analysis: Form IV.

Examples 50-54

Preparation of Varenicline Phosphate Form II

Varenicline phosphate (150 mg) was suspended in the solvent (quantity as indicated in the Table 6), and heated to reflux. The mixture was allowed to cool to ambient temperature, and stirred for 24 hours at this temperature before evaporation of the solvent. Results are summarized in Table 6.

TABLE 6

| Example | Solvent | Quantity (mL) | XRD Analysis |
| --- | --- | --- | --- |
| 50 | chloroform | 3 mL | Form II |
| 51 | MTBE | 3 mL | Form II |
| 52 | 2-butanone | 3 mL | Form II |
| 53 | Methyl i-butylketone | 3 mL | Form II |
| 54 | i-propyl acetate | 3 mL | Form II |

Example 55

Preparation of Varenicline Phosphate Form III

Varenicline phosphate (100 mg) was suspended in methanol (3 mL), and heated to reflux for 1 h. The suspension was allowed to cool to ambient temperature overnight. The solid was filtered and analysed by XRD. HPLC purity: 99.96%; XRD Analysis: Form III.

Example 56

Preparation of Varenicline Hydrochloride Form II

Varenicline base (2.3 g) was suspended in 20 mL of MTBE. Hydrochloric acid (1.1 g of 37% aqueous solution) was added and the mixture was stirred for 3 h at room temperature. The mixture was filtered and dried under vacuum at 40° C. XRD Analysis: Form II.

Examples 57-66

Preparation of Varenicline Hydrochloride Form III

Varenicline hydrochloride (150 mg) was suspended in the solvent (quantity as indicated in Table 9), and heated to reflux. In the case of ethanol, methanol and water/ethanol complete dissolution was observed. The mixture was allowed to cool to ambient temperature, and stirred for 24 hours at this temperature before evaporation of the solvent. Results are summarized in Table 7.

TABLE 7

| Example | Solvent | Quantity (mL) | Result |
| --- | --- | --- | --- |
| 57 | acetone | 3 mL | Form III |
| 58 | chloroform | 3 mL | Form III |
| 59 | methanol | 0.7 mL | Form III |
| 60 | MTBE | 3 mL | Form III |
| 61 | THF | 3 mL | Form III |
| 62 | ethanol | 3 mL | Form III |
| 63 | 2-butanone | 3 mL | Form III |
| 64 | Methyl i-butylketone | 3 mL | Form III |
| 65 | water/ethanol (20-80) | 0.7 mL | Form III |
| 66 | i-propyl acetate | 3 mL | Form III |

Example 67

Stability Studies of Varenicline Crystalline Salts

The varenicline crystalline salts were stored under standard conditions (i.e. room temperature, normal pressure, ambient atmosphere). The samples were analyzed after one year by HPLC and XRD. Results are summarized in Table 8.

TABLE 8

| Varenicline Salt | Purity (HPLC) % initial | % 1 year later | XRD result Initial | 1 year later |
|---|---|---|---|---|
| Maleate | 100 | 99.90 | Form I | Form I |
| Fumarate | 99.84 | 99.76 | Form I | Form I |
| Phosphate | 100 | 99.89 | Form I | Form I |
| Phosphate | 99.89 | 99.93 | Form II | Form II |
| Pyroglutamate | 99.99 | 99.83 | Form I | Form I |
| Hemi-Adipate | 99.89 | 99.77 | Form I | Form I |
| Galactarate | 99.91 | 99.71 | Form I | Form I |
| Malate | 99.94 | 99.66 | Form II | Form II |
| Malate | 99.95 | 99.47 | Form I | n.d.[a] |
| Glycolate | 99.95 | 99.57 | Form I | n.d.[a] |
| Hemi-1,2-ethane disulfonate | 99.97 | 99.36 | Form I | n.d.[a] |
| α-Ketoglutarate | 99.71 | 98.45 | Form I | n.d.[a] |
| DL-lactate | 98.98 | 98.48 | Form I | Form I with some changes |
| Glutarate | 98.77 | 97.90 | Form I | Form I with additional peaks. |
| di-Mesylate | 99.99 | 99.28 | Form I | Different form |
| Oxalate | 99.91 | 99.72 | Form I | low crystalline and different |
| Malonate | 99.91 | 99.45 | Form I | Very low crystalline. |
| Mandelate | 99.93 | 95.55 | Form I | Different form |
| Hydrochloride | 99.91 | 99.68 | Form II | Forms II + III |

[a] Not determined.

The invention claimed is:

1. A dicarboxylic acid salt form of varenicline wherein said dicarboxylic acid salt form is varenicline fumarate Form I, which shows an x-ray diffraction pattern (2θ) (±0.2°) having characteristics peaks at 10.6, 11.9, 13.2, 16.2, 16.6, 18.0, 21.5, 22.6, 25.7, 28.5 and 29.1°.

2. The dicarboxylic acid salt form of varenicline of claim 1, wherein said varenicline fumarate Form I shows an xray diffraction pattern (2θ) (±0.2°) having further characteristic peaks at 7.1, 11.2, 13.8, 14.4, 193, 20.5, 22.3, 24.1, 24.5, 24.9, 27.8 and 31.8°.

3. A process for preparing the varenicline fumarate Form I of claim 1, said process comprising contacting varenicline with fumaric acid in the presence of a solvent comprising (i) a $C_1$-$C_5$ alcohol, a ketone, a haloalkane, an ether, an ester, or a mixture thereof, or (ii) a mixture of water and one or more of a $C_1$-$C_5$ alcohol, to ketone, a haloalkane, an ether, and an ester, and optionally removing the solvent.

4. The process of claim 3, wherein the solvent is selected from the group consisting of acetone, 2-butanone, methyl isobutyl ketone, chloroform, methanol, ethanol, isopropyl alcohol, methyl tert-butyl ether, tetrahydrofuran, isopropyl acetate and ethanol/water (80:20).

* * * * *